US010301622B2

(12) United States Patent
Mirkin et al.

(10) Patent No.: US 10,301,622 B2
(45) Date of Patent: May 28, 2019

(54) QUANTIFICATION AND SPATIO-TEMPORAL TRACKING OF A TARGET USING A SPHERICAL NUCLEIC ACID (SNA)

(71) Applicant: NORTHWESTERN UNIVERSITY, Evanston, IL (US)

(72) Inventors: Chad A. Mirkin, Wilmette, IL (US); William E. Briley, Chicago, IL (US); Pratik S. Randeria, Hoffman Estates, IL (US); Nathaniel J. Kim, Carmel, IN (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 71 days.

(21) Appl. No.: 15/034,005

(22) PCT Filed: Nov. 4, 2014

(86) PCT No.: PCT/US2014/063921
§ 371 (c)(1),
(2) Date: May 3, 2016

(87) PCT Pub. No.: WO2015/066708
PCT Pub. Date: May 7, 2015

(65) Prior Publication Data
US 2016/0281086 A1    Sep. 29, 2016

Related U.S. Application Data

(60) Provisional application No. 61/899,528, filed on Nov. 4, 2013.

(51) Int. Cl.
*A61K 48/00* (2006.01)
*C12N 15/11* (2006.01)
(Continued)

(52) U.S. Cl.
CPC .......... *C12N 15/113* (2013.01); *C12Q 1/6823* (2013.01); *C12N 2310/14* (2013.01); *C12N 2310/3517* (2013.01)

(58) Field of Classification Search
CPC .. A61K 31/5377; A61K 9/143; A61K 31/192; C12N 15/85; C12N 15/87; C12N 2310/14; C12N 2310/3517
See application file for complete search history.

(56) References Cited

U.S. PATENT DOCUMENTS 3,687,808 A    8/1972 Merigan et al.
4,469,863 A    9/1984 Ts'o et al.
(Continued)

FOREIGN PATENT DOCUMENTS

EP        1072679 A2      1/2001
WO    WO-1997/12896 A1    4/1997
(Continued)

OTHER PUBLICATIONS

V. Kim (Genes and Development, 2006, vol. 20:1993-1997).*
(Continued)

*Primary Examiner* — Terra C Gibbs
(74) *Attorney, Agent, or Firm* — Marshall, Gerstein & Borun LLP

(57) ABSTRACT

The present invention relates to methods of detecting and tracking a target molecule using a nanoparticle wherein the nanoparticle comprises a polynucleotide that can specifically associate with the target molecule, and wherein the association results in a change in a detectable marker that can be measured after association with the target molecule.

22 Claims, 7 Drawing Sheets
Specification includes a Sequence Listing.

(51) Int. Cl.
*C07H 21/02* (2006.01)
*C07H 21/04* (2006.01)
*C12N 15/113* (2010.01)
*C12Q 1/6823* (2018.01)

(56) References Cited

U.S. PATENT DOCUMENTS

| | | |
|---|---|---|
| 4,476,301 A | 10/1984 | Imbach et al. |
| 4,489,055 A | 12/1984 | Couvreur et al. |
| 4,845,205 A | 7/1989 | Huynh Dinh et al. |
| 4,981,957 A | 1/1991 | Lebleu et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,367,066 A | 11/1994 | Urdea et al. |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,472,881 A | 12/1995 | Beebe et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,502,177 A | 3/1996 | Matteucci et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,555 A | 10/1996 | Froehler et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,714,331 A | 2/1998 | Buchardt et al. |
| 5,719,262 A | 2/1998 | Buchardt et al. |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,747 A | 8/1998 | Schally et al. |
| 5,830,653 A | 11/1998 | Froehler et al. |
| 6,005,096 A | 12/1999 | Matteucci et al. |
| 6,361,944 B1 | 3/2002 | Mirkin et al. |
| 6,506,564 B1 | 1/2003 | Mirkin et al. |
| 6,750,016 B2 | 6/2004 | Mirkin et al. |
| 6,767,702 B2 | 7/2004 | Mirkin et al. |
| 7,238,472 B2 | 7/2007 | Mirkin et al. |
| 7,611,728 B2 | 11/2009 | Kidane et al. |
| 8,507,200 B2 | 8/2013 | Mirkin et al. |
| 2002/0172953 A1 | 11/2002 | Mirkin et al. |
| 2003/0147966 A1 | 8/2003 | Franzen et al. |
| 2004/0219565 A1 | 11/2004 | Kauppinen et al. |
| 2012/0244230 A1 | 9/2012 | Mirkin et al. |
| 2012/0282186 A1 | 11/2012 | Mirkin et al. |

FOREIGN PATENT DOCUMENTS

| | | |
|---|---|---|
| WO | WO-1998/04740 A1 | 2/1998 |
| WO | WO-1998/39352 A1 | 9/1998 |
| WO | WO-1999/14226 A2 | 3/1999 |
| WO | WO-2001/000876 A1 | 1/2001 |
| WO | WO-2001/051665 A2 | 7/2001 |
| WO | WO-01/073123 A2 | 10/2001 |
| WO | WO-02/096262 A2 | 12/2002 |
| WO | WO-2007/111924 A2 | 10/2007 |

OTHER PUBLICATIONS

Patel et al. (Mol Pharm. 2011 vol. 8:1285-1291).*
Ahmadi, et al., "Shape-Controlled Synthesis of Colloidal Platinum Nanoparticles," Science, 272:1924-1926 (1996).
Allara, et al. "Spontaneously Organized Molecular Assemblies 1. Formation, Dynamics, and Physical Properties of n-Alkanoic Acids Adsorbed from Solution on an Oxidized Aluminum Surface," Langmuir 1:45-52 (1985).
Allara, et al. "The Study of the Gas-Solid Interaction of Acetic Acid with a Cuprous Oxide Surface Using Reflection-Absorption Spectroscopy," J. Colloid Interface Sci., 49:410-421 (1974).
Altschul et al., "Basic Local Alignment Search Tool," *J. Mol. Biol.*, 215:403-410 (1990).
Bartlett, "Fluorescence in Sity Hybridization," Mol. Diag. Cancer 97:77-87 (2004).
Bassell, et al., "Fragile X Syndrome: Loss of Local mRNA Regulation Alters Synaptic Development and Function," Neuron 60, 201 (2008).

(56) References Cited

OTHER PUBLICATIONS

Burwell, "Modified silica gels as adsorbents and catalysts," Chemical Technology, 4: 370-377 (1974).
Charreyre et al., "Fluorescence Energy Transfer Study of the Conformation of Oligonucleotides Covalently Bound to Polystyrene Latex Particles," Langmuir, 13: 3103-3110 (1997).
Chrisey et al., "Covalent attachment of synthetic DNA to self-assembled monolayer films," Nucleic Acids Research, 24: 3031-3039 (1996).
Cook, "Medicinal chemistry of antisense oligonucleotides—future opportunities," Anti-Cancer Drug Design , 6: 585-607 (1991).
Curtis, et al. "A morphology-Selective Copper Organosol," *Angew. Chem. Int. Ed. Engl.*, 27:1530-1533 (1988).
De Mesmaeker et. al., "Backbone modification in oligonucleotides and peptide nucleic acid systems," Current Opinion in Structural Biology, 5: 343-355 (1995).
Elaissari et al., "Effect of Charge Nature on the Adsorption of Single-Stranded DNA Fragments onto Latex Particles," J. Colloid Interface Sci., 202: 251-260 (1998).
Eltekova, et al. "Adsorption of Aromatic Compounds from Solutions on Titanium Dioxice and Silica," Langmuir, 3: 951-957 (1987).
Englisch et al., "Chemically Modified Oligonucleotides as Probes and Inhibitors," *Angewandte Chemie*, International Edition, 30: 613-722 (1991).
Enustun, et al. "Coagulatin of Colloidal Gold," J. Am. Chem. Soc. 85: 3317-3328 (1963).
F. Eckstein (ed.) Oligonucleotides and Analogues, 1st Ed. (Oxford University Press, New York, 1991).
Fahy et al., "Design and synthesis of polyacrylamide-based oligonucleotide supports for use in nucleic acid diagnostics," Nucleic Acids Research, 21: 1819-1826 (1993).
Fattal, et al., "Biodegradable polyalkylcyanoacrylate nanoparticles for the delivery of oligonucleotides," J. Controlled Release 53: 137-143 (1998).
Freier et al., "The ups and downs of nucleic acid duplex stability: structure-stability studies on chemically-modified DNA:RNA duplexes," Nucleic Acids Research, 25:4429-4443 (1997).
Grabar et al., "Preparation and Characterization of Au Colloid Monolayers," Anal. Chem., 67: 735-743 (1995).
Hayashi, "Ultrafine Particles," Physics Today, pp. 44-60 (1987).
Hayashi, "Ultrafine Particles," Vac. Sci. Technol. A5(4):1375-84 (1987).
Hayat, M. A. (ed.) Colloidal Gold: Principles, Methods, and Applications (Academic Press, San Diego, 1991).
Henglein, et al., "Absorption Spectrum and Some Chemical Reactions of Colloidal Platinum in Aqueous Solution," J. Phys. Chem., 99:14129-14136 (1995).
Hickman et al., "Combining Spontaneous Molecular Assembly with Microfavrication to Pattern Surfaces: Selective Binding of Isonitriles to Platinum Microwires and Characterization by Electrochemistry and Surface Spectroscopy," J. Am. Chem. Soc., 111:7271-7272 (1989).
Hubbard, "Electrochemistry of Well-Defined Surfaces," Acc. Chem. Res., 13:177-184 (1980).
Iler, The Chemistry of Silica, Chapter 6, (Wiley 1979).
International Search Report and Written Opinion from PCT/US2014/63921 dated Mar. 4, 2015.
Jansen, "mRNA Localization: Message on the Move," Nat Rev Mol Cell Biol 2: 247-256 (2001).
Kolarova et al., "Isolation of 3.5-kb Fragments on Magnetic Solid Supports," Biotechniques, 20:196-198 (1996).
Kukowska-Latallo, et al., "Efficient transfer of genetic material into mammalian cells using Starburst polyamidoamine dendrimers," Proc. Natl. Acad. Sci. USA 93:4897-4902 (1996).
Lee et al., "Adsorption of Ordered Zirconium Phosphonate Multilayer Films on Silicon and Gold Surfaces," J. Phys. Chem., 92: 2597-2601 (1988).
Liu, et al., "New Poly(D-glucaramidoamine)s Induce DNa Nanoparticle Formation and Efficient Gene Delivery into Mammalian Cells," J. Am. Chem. Soc. 126:7422-7423 (2004).
Liu-Yesucevitz et al., "Local RNa Translation at the Synapse and in Disease," The Journal of Neuroscience 31: 16086-16093 (2011).
Maoz, "Penetration-Controlled Reactions in Organized Monolayer Assemblies. 2. Aqueous Permanganate Interaction with Self-Assembling Monolayers of Long-Chain Surfactants," Langmuir, 3: 1045-1051 (1987).
Maoz, et al. "Penetration-Controlled Reactions in Organized Monolayer Assemblies. 1. Aqueous Permanganate Interaction with Monolayer and Multilayer Films of Long-Chain Surfactants," Langmuir, 3: 1034-1044 (1987).
Marinakos et al., "Gold Nanoparticles as Templates for the Synthesis of Hollow Nanometer-Sized Conductive Polymer Capsules," Adv. Mater. 11:34-37 (1999).
Marinakos et al., "Template Synthesis of One-Dimensional Au, Au-Poly(pyrrole), and Poly(pyrrole) Nanoparticle Arrays," Chem. Mater. 10: 1214-19 (1998).
Martin et al., "New Access to 2'-O-Alkylated Ribonucleosides and Properties of 2'-O-Alkylated Oligoribonucleotides," Helv. Chim. Acta, 78: 486-504 (1995).
Massart, R., "Preparation of Aqueous Magnetic Liquids in Alkaline and Acidic Media," IEEE Transactions on Magnetics, 17:1247-1248 (1981).
Massich et al., "Cellular Response of Polyvalent Oligonucleotide-Gold Nanoparticle Conjugates," ACS Nano 4:5641-5646 (2010).
Massich et al., "Regulating Immune Response Using Polyvalent Nucleic Acid-Gold Nanoparticle Conjugates," Molecular Pharmaceutics 6:1934-1940 (2009).
Matteucci, et al. "Synthesis of Deoxyoligonucleotides on a Polymer Support," J. Am. Chem. Soc., 103: 3185-3191 (1981).
MRS Bulletin, Jan. 1990, pp. 16-47.
Mucic et al., "Synthesis and characterization of DNa with ferrocenyl groups attached to their 5'-termini: electrochemical characterization of a redox-active nucleotide monolayer," Chem. Commun. 555-557 (1996).
Nielsen et al., "Sequence-Selective Recognition of DNA by Strand Displacement with a Thymine-Substituted Polyamide," Science, 254:1497-1500 (1991).
Nuzzo et al., "Spontaneously Organized Molecular Assemblies. 3. Preparation and Properties of Solution Adsorbed Monolayers of Organic Disulfides on Gold Surfaces," J. Am. Chem. Soc., 109: 2358-2368 (1987).
Oleynikov et al., "Real-Time Visualization of ZBP1 Association with γ-Actin nRNA during Transcription and Localization," Current Biology 13:199-207 (2003).
Prigodich et al., "Multiplexed Nano-flares: mRNA Detection in Live Cells," Analytical Chemistry 84:2062-2066 (2012).
Prigodich, et al., "Nano-Flares for mRNA Regulation and Detection," ACS Nano 3:2147-2152 (2009).
Rosi et al., Oligonucleotide-Modified Gold Nanoparticles for Intracellular Gene Regulation<' Science 312: 1027-1030 (2006).
Sambrook et al., Molecular Cloning: A Laboratory Manual (2nd ed. 1989).
Sanghvi, Y. S., Chapter 15, Antisense Research and Applications, pp. 274-288, Crooke, S. T. and Lebleu, B., ed., CRC Press, 1993.
Santangelo et al., "Dual FRET molecular beacons for mRNA detection in living cells," Nucleic Acids Research 32(e57):1-9 (2004).
Schmid, G. (ed.) Clusters and Colloids (VCH, Weinheim, 1994).
Seferos et al., "Nano-Flares: Probes for Transfection and mRNA Detection in Living Cells," Journal of the American Chemical Society 129:15477-15479 (2007).
Shestakova, et al. "Correlation of γ-Actin Messenger RNA Localization with Metastatic Potential in Rat Adenocarcinoma Cells Lines," Cancer Research, 59:1202-1205 (1999).
Soriaga, et al. "Determination of the Orientation of Aromatic Molecules Adsorbed on Platinum Electrodes. The Effect of Solute Concentration," J. Am. Chem. Soc., 104:3937-3945 (1982).
The Concise Encyclopedia of Polymer Science and Engineering, pp. 858-859, Kroschwitz, J. I., ed. John Wiley & Sons, 1990.

(56) References Cited

OTHER PUBLICATIONS

Thomas et al., "Synaptic control of local translation: the plot thickens with new characters," Cell. Mol. Life Sci. 71: 2219 (2014).
Timmons, et al. "Investigation of Fatty Acid Monolayers on Metals by Contact," J. Phys. Chem., 69:984-990 (1965).
Tondelli, et al., "Highly efficiency cellular uptake of c-myb antisense oligonucleotides through specifically designed polymeric nanospheres," Nucl. Acids Res. 26:5425-5431 (1998).
Wasserman et al., "Structure and Reactivity of Alkylsiloxane Monolayers Formed by Reaction of Alkyltrichlorosilanes on Silicon Substrates," Langmuir, 5: 1074-1087 (1989).
Weiler et al., "Fragile X mental retardation protein is translated near synapses in response to neorotransmitter activation," Proceedings of the National Academy of Sciences 94: 5395-5400 (1997).
Whitesides, 1995, Proceedings of the Robert A. Welch Foundation 39th Conference on Chemical Research Nanophase Chemistry, Houston, Tex., pp. 109-121.
Wolf et al., "Rapid hybridization kinetics of DNA attached to submicron latex particles," Nucleic Acids Research, 15:2911-2926 (1987).
Zhang, et al. "Antibody-Linked Spherical Nucleic Acids for Cellular Targeting," J. Am. Chem. Soc. 16488-16491 (2012).
Zhang, et al. "PowerBLAST: A New Network Blast Application for Interactive or Automated Sequence Analysis and Annotation," Genome Res., 7: 649-656 (1997).

\* cited by examiner

QUANTIFICATION AND SPATIO-TEMPORAL TRACKING OF A TARGET USING A SPHERICAL NUCLEIC ACID (SNA)

CROSS REFERENCE TO RELATED APPLICATIONS

This application is a U.S. National Phase of PCT/US2014/063921, filed Nov. 4, 2014, which claims the priority benefit under 35 U.S.C. § 119(e) of U.S. Provisional Patent Application No. 61/899,528, filed Nov. 4, 2013, the disclosures of which are incorporated herein by reference in their entirety.

STATEMENT OF GOVERNMENT INTEREST

This invention was made with government support under U54 CA151880 awarded by the National Institutes of Health. The government has certain rights in the invention.

SEQUENCE LISTING

This application contains, as a separate part of the disclosure, a Sequence Listing in computer-readable form (filename: 2012-078PC_SeqListing.txt; created: Nov. 4, 2014; 3,342 bytes—ASCII text file) which is incorporated by reference in its entirety.

FIELD OF THE INVENTION

The present invention relates to methods of detecting and tracking a target molecule using a nanoparticle wherein the nanoparticle comprises a polynucleotide that can specifically associate with the target molecule, and wherein the association results in a change in a detectable marker that can be measured after association with the target molecule.

BACKGROUND OF THE INVENTION

The study of RNA is critical for applications in basic biology and in the diagnosis and treatment of disease. Recently, researchers have determined that the translation of many mRNA sequences relies not only on proper quantities of mRNA expression, but also the active transport of transcripts to subcellular compartments where highly localized translation can occur [Jansen, Nat Rev Mol Cell Biol 2: 247 (2001)]. For example, Beta-actin localizes at the leading lamellae of growing fibroblasts, driving cell motility [Oleynikov et al., Current Biology 13: 199 (2003)]. Unfortunately, despite the importance of these two aspects in mRNA function, there is no tool available to both measure intracellular concentration and observe localization of mRNA in live cells. The NanoFlare (NF) architecture, a Spherical Nucleic Acid (SNA) construct capable of determining relative mRNA concentration levels in live cells has previously been described [Seferos et al., Journal of the American Chemical Society 129; 15477 (2007); Prigodich et al., Analytical Chemistry 84: 2062 (2012); Rosi et al., Science 312: 1027 (2006); Prigodich et al., ACS Nano 3, 2147 (2009)].

The study of RNA is a critical component of biological research and in the diagnosis and treatment of disease. Recently, the localization of mRNA has emerged as an essential process for a number of cellular processes, including restricting certain proteins to specific compartments within cells [Thomas et al., Cell. Mol. Life Sci. 71: 2219 (2014)]. For instance, synaptic potentiation, the basis of learning and memory, relies upon the local translation of specific mRNAs in pre- and post-synaptic compartments [Weiler et al., Proceedings of the National Academy of Sciences 94: 5395 (1997)]. Likewise, the misregulation of RNA distribution is associated with many disorders, ranging from mental retardation and autism to cancer metastasis [Liu-Yesucevitz et al., The Journal of Neuroscience 31: 16086 (2011); Bassell et al., Neuron 60, 201 (2008); Shestakova, E. A.; Wyckoff, J.; Jones, J.; Singer, R. H.; Condeelis, J. Cancer Research 1999, 59, 1202]. However, despite the significant role of mRNA transport and localization in cellular function, the available methods to visualize these phenomena are severely limited. For example, Fluorescence In Situ Hybridization (FISH), the most commonly used technique to analyze spatial distribution of RNA, requires fixation and permeabilization of cells prior to analysis. As a result, analysis of dynamic RNA distribution is restricted to a single snapshot in time. With such a limitation, understanding the translocation of RNA with respect to time, cell cycle, or external stimulus is difficult or impossible. Further, fixed cell analysis is a highly specialized procedure, due to the number steps necessary to prepare a sample. Fixation, permeabilization, blocking, and staining processes each require optimization and vary based on cell type and treatment conditions, rendering FISH prohibitively complicated in many cases. Likewise, live cell analysis platforms such as molecular beacons require harmful transfection techniques such as microinjection or lipid transfection, and are rapidly sequestered to the nucleus upon cellular entry. Thus, in order to accurately study the dynamics of intracellular RNA, a new type of analysis platform is required.

SUMMARY OF THE INVENTION

The disclosure provides compositions and methods for determining the intracellular concentration of a target molecule and/or spatio-temporally tracking the target molecule comprising contacting a target polynucleotide with a composition comprising a nanoparticle under conditions that allow association of the target polynucleotide with the nanoparticle, the nanoparticle comprising a first polynucleotide attached thereto, wherein a portion of the first polynucleotide comprises a sequence that is identical to a portion of the target polynucleotide, the nanoparticle further comprising a second polynucleotide, wherein the second polynucleotide: (i) comprises a marker; and (ii) is hybridized to the first polynucleotide; wherein association of the target polynucleotide and the nanoparticle results in: (i) release of the second polynucleotide from the nanoparticle; and (ii) association of the second polynucleotide and the target polynucleotide, the association causing a detectable signal.

In some embodiments, the position of the signal is determined. In further embodiments, the detectable signal is measured at time X and at time Y, wherein time Y is subsequent to time X. In still further embodiments, the position of the signal is determined at time X and at time Y. In yet additional embodiments, the change in position between time X and time Y is determined.

In some embodiments, the detectable signal is measured in vitro, while in other embodiments, the detectable signal is measured in vivo. In related embodiments, the detectable signal is measured in a cell and/or a tissue. In further embodiments, the cell and/or tissue is fixed. In still further embodiments, the fixed cell and/or tissue is permeabilized. In yet additional embodiments, the cell and/or tissue is fixed and permeabilized.

In further embodiments of the methods, the first polynucleotide and/or the second polynucleotide is DNA. In some embodiments, the first polynucleotide and/or the second polynucleotide is RNA.

The marker, in various embodiments, is quenched when the second polynucleotide comprising the marker is hybridized to the first polynucleotide. In some embodiments, the second polynucleotide comprises a marker which is a detectable label, wherein the marker is detectable only when the second polynucleotide is associated with the target polynucleotide.

The nanoparticle, in some embodiments, comprises a multiplicity of first polynucleotides and a multiplicity of second polynucleotides. In further embodiments, each polynucleotide in the multiplicity of second polynucleotides associate with the same target polynucleotide. In still further embodiments, at least one polynucleotide in the multiplicity of second polynucleotides associates with a different target polynucleotide than at least one other polynucleotide in the multiplicity of second polynucleotides.

In some embodiments, the target polynucleotide is a non-coding RNA, and in further embodiments, the non-coding RNA is a piwi-interacting RNA (piRNA).

The disclosure also contemplates that in some embodiments, the composition further comprises a therapeutic agent. In further embodiments, the composition further comprises a regulatory polynucleotide. The regulatory polynucleotide, in various embodiments, is selected from the group consisting of small interfering RNA (siRNA), piwi-interacting RNA (piRNA), and microRNA (miRNA).

In some embodiments, the first polynucleotide is between about 5 and about 30 bases in length.

In additional embodiments, the second polynucleotide is between about 10 and about 60 bases in length.

The second polynucleotide, in various embodiments, hybridizes over the entire length of the first polynucleotide. In some embodiments, the second polynucleotide hybridizes over the entire portion of the first polynucleotide that is the same sequence as at least a portion of the target polynucleotide. In further embodiments, hybridization of the second polynucleotide to the first polynucleotide results in an overhang of the second polynucleotide, wherein the overhang is from about 2 to about 30 nucleotides in length.

The nanoparticle, in further embodiments, comprises about 10 second polynucleotides. In some embodiments, the difference in melting temperature ($T_m$) between the first polynucleotide and the second polynucleotide is about 20-25° C.

DETAILED DESCRIPTION OF THE INVENTION

Figure 1:
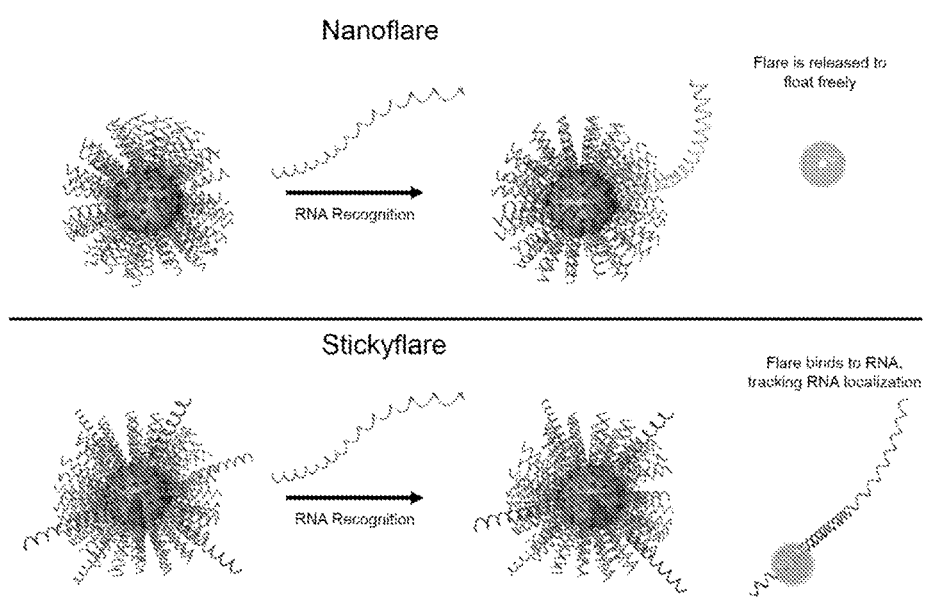
FIG. 1 is a schematic depicting operational differences between Nanoflare and Stickyflare. In Nanoflare (top), the nanoparticle binds to oligonucleotide target and releases the nanoflare to float freely while the target remains bound to the nanoparticle. In contrast, flares from the stickyflare (bottom) are complementary to oligonucleotide targets, which allow them to bind to the target and act as a fluorescent label for location and mobility of the target, i.e. intracellular tracking.

The present disclosure is directed to a nanoparticle-polynucleotide conjugate, termed the Stickyflare (SF), which enables facile quantification of RNA expression in live cells, and spatio-temporal analysis of RNA transport and localization. Such a platform allows for, inter alia, the quantification of transcript expression, and the ability to track RNA in real-time in a single cell, without the need for transfection agents or specialized techniques.

The Stickyflare was derived from the successful architecture of the Nanoflare (see U.S. Pat. No. 8,507,200, incorporated by reference herein in its entirety), and is capable of entering live cells without the need for transfection agents and recognizing target RNA transcripts in a sequence-specific manner. The Nanoflare comprises a 13 nanometer (nm) gold nanoparticle core functionalized with a densely packed, highly oriented shell of oligonucleotides designed to be antisense to a target RNA transcript. A fluorophore-conjugated reporter strand, termed the flare, is subsequently hybridized to the antisense oligonucleotides via complementary base pairing. Hybridization of the flare holds the fluorophore in close proximity to the gold core of the SNA, effectively quenching fluorescence. However, upon cellular entry the antisense capture sequences of the Nanoflare bind to targeted transcripts, forming a longer, more stable duplex. This binding event displaces the flare from the gold surface, resulting in quantifiable fluorescence, the intensity of which is directly related to the expression level of the target RNA. This process requires little specialization, as the Nanoflare enters live cells via endocytosis without the need for harmful transfection techniques, and with negligible cytotoxicity and immunogenicity. As a result, the Nanoflare has grown into a powerful and prolific tool in biology and medical diagnostics, with over 1700 unique forms commercially available today [Massich et al., Molecular Pharmaceutics 6: 1934 (2009); Massich et al., ACS Nano 4: 5641 (2010)].

In contrast to the Nanoflare, and upon recognition of a target molecule, the Stickyflare transfers a detectable marker-conjugated reporter to the transcript, resulting in a "turning on" of the detectable marker in a quantifiable manner, and the labeling of targeted transcripts, allowing the RNA to be tracked via microscopy as it is transported throughout the cell. This SNA is used, in various aspects, to analyze the expression level and spatial distribution of mRNA in a cell and to observe the real-time transport of the mRNA. Further, the disclosure also allows for the tracking of transcripts that undergo more extensive compartmentalization.

The StickyFlare allows for spatio-temporal tracking of target mRNA in live cells. In addition, the nontoxic nature of the SNA construct allows for real-time observation of dynamic RNA movement [Massich et al., Mol Pharm 6: 1934 (2009); Massich et al., ACS Nano 4: 5641 (2010)]. It is important to note that the Nanoflare architecture does not lend itself well to the tracking of a target molecule such as RNA. The short flares in the NF technology do not just release and then float freely—they are relatively short polynucleotides and they can therefore bind nonspecifically to many off-target molecules. Thus, the flare would be released and as soon as it came into contact with any off-target molecules it would bind on to them and track the non-target molecule.

Among the advantages of the methods disclosed herein are: (1) markers such as fluorophores can be delivered into the cytoplasm of cells in high concentrations without disrupting cellular function. This is a marked improvement on molecular beacon technology, which must be microinjected in order to be present at sufficient concentrations. (2) The SNA architecture is resistant to nucleases, meaning lower background fluorescence from degraded marker-containing nucleotides. (3) The SNA architecture triggers virtually no immune response, meaning RNA localization is determined without interruption to cellular function. (4) Hybridization to a target sequence using antisense DNA is significantly more specific when the DNA is present in the SNA structure, compared to free DNA. Thus the disclosure provides methods for intracellular quantification of mRNA and spatio-temporal tracking of mRNA.

"Stickyflare" and "spherical nucleic acid" as used herein refer to a polynucleotide-functionalized nanoparticle as described in the disclosure.

As used herein, the term "specifically recognizes" or "specifically associates" means that a polynucleotide can identify and/or interact with a target molecule with a higher affinity and/or avidity compared to a non-target molecule.

"Melting temperature ($T_m$)," as used herein, is understood in the art and is a predicted value based on a polynucleotide concentration of 0.25 uM and a Na concentration of 50 mM.

Stickyflare Technology

Historically, antisense oligonucleotides have not been successful at tracking mRNA in live cells. A number of researchers have tried using molecular beacons—transfected DNA hairpins designed to be antisense to a target gene—and have run into significant obstacles. Within minutes of transfection, DNA molecular beacons are sequestered into the nucleus. Once there, the molecular beacons exhibit an unavoidable DNA degradation, resulting in a very high concentration of unquenched molecular beacons in the nucleus. This, combined with the fact that even intact molecular beacons are not perfectly quenched, results in a significant false-positive signal in the nucleus that renders antisense technique virtually useless, or in many cases worse than useless since false data is worse than no data. Stickyflares, by contrast, overcome such limitations.

Without wishing to be bound by theory, the Stickyflare is bound to the particle and, as a result, is not sequestered in the nucleus. The Nanoflare technology has already demonstrated that when released to float freely, single stranded flares do not go into the nucleus. However, the sequestration of molecular beacons indicates that double-stranded DNA oligonucleotides are recognized and actively transported. Thus, it is possible that the DNA duplex of the Stickyflare would be similarly recognized and transported, were it not for the fact that the nanoparticle that it is attached to is many times larger than anything that is allowed into the nucleus. Further, the high local salt concentration around the nanoparticle likely inhibits the recognition of DNA duplexes by these proteins. The net effect is that the Stickyflares cannot be transported to the nucleus when bound to the SNA. Once the flare is pulled away from the SNA, however, it is attached to the target molecule and goes wherever the target goes, including into the nucleus if nuclear RNA is targeted.

Architecture

The compositions and methods provided herein function under the principle that a polynucleotide is directly or indirectly labeled with a marker, and association of the polynucleotide with a target molecule results in the marker becoming detectable, or more detectable. Accordingly, when the polynucleotide is not associated with the target molecule, the marker is relatively undetectable, or quenched. While it is understood in the art that the term "quench" or "quenching" is often associated with fluorescent markers, it is contemplated herein that the signal of any marker is quenched when it is relatively undetectable. Thus, it is to be understood that methods described and/or exemplified throughout this description that employ fluorescent markers are provided only as single embodiments of the methods contemplated, and that any marker that can be quenched may be substituted for the exemplary fluorescent marker.

In one aspect, a marker as disclosed herein is a label attached directly to the second polynucleotide, this second polynucleotide having a lower binding affinity or binding avidity for the first polynucleotide that is functionalized to a nanoparticle, such that association of the target molecule with the second polynucleotide causes the second polynucleotide to be displaced from its association with the first polynucleotide. According to the disclosure, the marker is present on a second polynucleotide which can hybridize to the first polynucleotide that is functionalized to a nanoparticle in a position such that the marker is in sufficient proximity to the nanoparticle that the nanoparticle exerts its quenching effect. When the second polynucleotide recognizes and associates with a target molecule, the hybridized and labeled second polynucleotide is displaced from the first polynucleotide, and the quenching effect of the nanoparticle is abated.

First polynucleotide: the first polynucleotide is the polynucleotide that is functionalized to the nanoparticle. In one embodiment, the first polynucleotide is from about 5 to about 30 nucleotides in length. In further embodiments, the first polynucleotide is from about 5 to about 10, or from about 5 to about 8, or from about 10 to about 20, or from about 10 to about 15 nucleotides in length. In still further embodiments, the first polynucleotide is at least about 5, at least about 10, or at least about 20 nucleotides in length. In specific embodiments, the first polynucleotide is or is at least 5, 6, 7, 8, 9, 10, 11, 12, 13, 14, 15, 16, 17, 18, 19, 20, 21, 22, 23, 24, 25, 26, 27, 28, 29, 30, or more nucleotides in length.

The melting temperature ($T_m$) of the first polynucleotide is, in various embodiments, from about 25° C. to about 50° C., or from about 25° C. to about 45° C., or from about 25° C. to about 30° C., or from about 30° C. to about 50° C., or from about 30° C. to about 45° C., or from about 30° C. to about 40° C., or from about 30° C. to about 35° C., or from about 35° C. to about 50° C., or from about 35° C. to about 45° C., or from about 35° C. to about 40° C., or from about 40° C. to about 50° C., or from about 40° C. to about 45° C. In further embodiments, the $T_m$ of the first polynucleotide is about 25° C., about 30° C., about 35° C., about 40° C., about 45° C., or about 50° C. One of skill in the art can routinely determine the $T_m$ of a given polynucleotide using, for example, computer software such as the "OligoAnalyzer" available on the Integrated DNA Technologies, Inc. (IDT) website.

Second Polynucleotide. the second polynucleotide is the polynucleotide that is hybridized to the first polynucleotide. As used herein, the second polynucleotide is "flare." In one embodiment, the second polynucleotide is from about 5 to about 60 nucleotides in length. In further embodiments, the second polynucleotide is from about 5 to about 50, or from about 5 to about 40, or from about 5 to about 30, or from about 5 to about 20, or from about 5 to about 10, or from about 10 to about 50, or from about 10 to about 40, or from about 10 to about 30, or from about 10 to about 20, or from about 20 to about 50, or from about 20 to about 40, or from about 20 to about 30, or from about 30 to about 50, or from about 30 to about 40 nucleotides in length. In still further embodiments, the second polynucleotide is at least about 5, at least about 10, at least about 20, at least about 30, at least about 40, or at least about 50 nucleotides in length. In specific embodiments, the second polynucleotide is or is at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or more nucleotides in length.

The first polynucleotide and/or the second polynucleotide is DNA, RNA, or any oligonucleotide analogue disclosed herein (including, but not limited to, a locked nucleic acid (LNA), 2'O-Me RNA, a peptide nucleic acid (PNA), or PS-DNA).

The melting temperature ($T_m$) of the second polynucleotide is, in various embodiments, from about 25° C. to about 80° C., or from about 25° C. to about 75° C., or from about 25° C. to about 70° C., or from about 25° C. to about 65° C., or from about 25° C. to about 60° C., or from about 25° C. to about 55° C., or from about 25° C. to about 50° C., or from about 25° C. to about 45° C., or from about 25° C. to about 40° C., or from about 25° C. to about 35° C., or from about 25° C. to about 30° C., or from about 30° C. to about 80° C., or from about 30° C. to about 75° C., or from about 30° C. to about 70° C., or from about 30° C. to about 65° C., or from about 30° C. to about 60° C., or from about 30° C. to about 55° C., or from about 30° C. to about 50° C., or from about 30° C. to about 45° C., or from about 30° C. to about 40° C., or from about 30° C. to about 35° C., or from about 35° C. to about 80° C., or from about 35° C. to about 75° C., or from about 35° C. to about 70° C., or from about 35° C. to about 65° C., or from about 35° C. to about 60° C., or from about 35° C. to about 55° C., or from about 35° C. to about 50° C., or from about 35° C. to about 45° C., or from about 35° C. to about 40° C., or from about 40° C. to about 80° C., or from about 40° C. to about 75° C., or from about 40° C. to about 70° C., or from about 40° C. to about 65° C., or from about 40° C. to about 60° C., or from about 40° C. to about 55° C., or from about 40° C. to about 50° C., or from about 40° C. to about 45° C., or from about 45° C. to about 80° C., or from about 45° C. to about 75° C., or from about 45° C. to about 70° C., or from about 45° C. to about 65° C., or from about 45° C. to about 60° C., or from about 45° C. to about 55° C., or from about 45° C. to about 50° C., or from about 50° C. to about 80° C., or from about 50° C. to about 75° C., or from about 50° C. to about 70° C., or from about 50° C. to about 65° C., or from about 50° C. to about 60° C., or from about 50° C. to about 55° C., or from about 55° C. to about 80° C., or from about 55° C. to about 75° C., or from about 55° C. to about 70° C., or from about 55° C. to about 65° C., or from about 55° C. to about 50° C., or from about 60° C. to about 80° C., or from about 60° C. to about 75° C., or from about 60° C. to about 70° C., or from about 60° C. to about 65° C., or from about 65° C. to about 80° C., or from about 65° C. to about 75° C., or from about 65° C. to about 70° C., or from about 70° C. to about 80° C., or from about 70° C. to about 75° C., or from about 75° C. to about 80° C. In further embodiments, the $T_m$ of the second polynucleotide is about 25° C., about 30° C., about 35° C., about 40° C., about 45° C., about 50° C., about 55° C., about 60° C., about 65° C., about 70° C., about 75° C., or about 80° C. In still further embodiments, the $T_m$ of the second polynucleotide is at least about 25° C., at least about 30° C., at least about 35° C., at least about 40° C., at least about 45° C., at least about 50° C., at least about 55° C., at least about 60° C., at least about 65° C., at least about 70° C., at least about 75° C., or at least about 80° C.

Relationship Between the First Nucleotide and the Second Nucleotide. In additional embodiments, determination of the optimal length of the first polynucleotide and the second polynucleotide is accomplished by designing the first polynucleotide and the second polynucleotide such that the second polynucleotide is always longer than the first polynucleotide. In various embodiments, the second polynucleotide is or is at least 1, is or is at least 2, is or is at least 3, is or is at least 4, is or is at least 5, is or is at least 6, is or is at least 7, is or is at least 8, is or is at least 9, is or is at least 10, is or is at least 11, is or is at least 12, is or is at least 13, is or is at least 14, is or is at least 15, is or is at least 16, is or is at least 17, is or is at least 18, is or is at least 19, is or is at least 20, is or is at least 21, is or is at least 22, is or is at least 23, is or is at least 24, is or is at least 25, is or is at least 26, is or is at least 27, is or is at least 28, is or is at least 29, is or is at least 30, is or is at least 31, is or is at least 32, is or is at least 33, is or is at least 34, is or is at least 35, is or is at least 36, is or is at least 37, is or is at least 38, is or is at least 39, is or is at least 40, is or is at least 41, is or is at least 42, is or is at least 43, is or is at least 44, is or is at least 45, is or is at least 46, is or is at least 47, is or is at least 48, is or is at least 49, is or is at least 50 or more nucleotides greater in length relative to the first polynucleotide. In further embodiments, the second polynucleotide is from about 1 to about 50, or from about 1 to about 40, or from about 1 to about 30, or from about 1 to about 20, or from about 1 to about 10, or from 1 to about 5, or from about 5 to about 50, or from about 5 to about 40, or from about 5 to about 30, or from about 5 to about 20, or from about 5 to about 10, or from about 10 to about 50, or from about 10 to about 40, or from about 10 to about 30, or from about 10 to about 20, or from about 15 to about 50, or from about 15 to about 40, or from about 15 to about 30, or from about 15 to about 20, or from about 20 to about 50, or from about 20 to about 40, or from about 20 to about 30, or from about 30 to about 50, or from about 40 to about 50 nucleotides greater in length relative to the first polynucleotide.

In some embodiments, the sequences of the first polynucleotide and the second polynucleotide are chosen such that the difference in $T_m$ between the first polynucleotide and the second polynucleotide is or is about 20° C. By way of example, the nucleotide sequence of the first polynucleotide yields a $T_m$ of 50° C., and the nucleotide sequence of the second polynucleotide yields a $T_m$ of 70° C., thus resulting in a difference in $T_m$ of 20° C. In further embodiments, the sequences of the first polynucleotide and the second polynucleotide are chosen such that the difference in $T_m$ between the first polynucleotide and the second polynucleotide is or is about 5° C., is or is about 10° C., is or is about 15° C., is or is about 25° C., or is or is about 30° C. In still further embodiments, the sequences of the first polynucleotide and the second polynucleotide are chosen such that the difference in $T_m$ between the first polynucleotide and the second polynucleotide is from about 5° C. to about 30° C., or from about 5° C. to about 25° C., or from about 5° C. to about 20° C., or from about 5° C. to about 15° C., or from about 5° C. to about 10° C., or from about 10° C. to about 30° C., or from about 10° C. to about 25° C., or from about 10° C. to about 20° C., or from about 10° C. to about 15° C., from about 15° C. to about 30° C., or from about 15° C. to about 25° C., or from about 15° C. to about 20° C., or from about 20° C. to about 30° C., or from about 20° C. to about 25° C.

In further embodiments, hybridization of the second polynucleotide to the first polynucleotide results in an overhang of the second polynucleotide, wherein the overhang is from about 2 to about 30 nucleotides in length. In various embodiments, the overhang is from about 2 to about 25, or from about 2 to about 20, or from about 2 to about 15, or from about 2 to about 10, or from about 2 to about 5, or from about 5 to about 30, or from about 5 to about 25, or from about 5 to about 20, or from about 5 to about 15, or from about 5 to about 10, or from about 10 to about 30, or from about 10 to about 25, or from about 10 to about 20, or from about 10 to about 15, or from about 15 to about 30, or from about 15 to about 25 or from about 15 to about 20, or from about 20 to about 30, or from about 20 to about 25, or from about 25 to about 30 nucleotides in length. In specific embodiments, hybridization of the second polynucleotide to the first polynucleotide results in an overhang of the second polynucleotide, wherein the overhang is or is at least 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides in length.

Hybridization

It is contemplated that, in various embodiments, the degree of hybridization between the first polynucleotide and the second polynucleotide is over the entire length of the first polynucleotide. In some embodiments, the second polynucleotide hybridizes over the entire portion of the first polynucleotide that is the same sequence as at least a portion of the target polynucleotide. In other words, the second polynucleotide hybridizes over the entire length of the first polynucleotide that is not part of the spacer sequence as defined herein. Thus, in some embodiments, the second polynucleotide does not hybridize to the full length of the first polynucleotide. In such embodiments, it is contemplated that the second polynucleotide hybridizes to about 70%, about 80%, about 90%, about 95% or more of the length of the first polynucleotide.

The degree of complementarity between the first polynucleotide and the second polynucleotide is contemplated, in various embodiments, to be about 50%, about 60%, about 70%, about 80%, about 90%, about 95% or more.

SF Applications in the Nucleus. In some aspects, the flare portion of the stickyflare enters the nucleus and, once in the nucleus, is used to bind promoter regions, or proteins involved in transcription or chromatin remodeling, in order to silence gene expression. In addition, by binding pre-mRNA or pri-miRNA inside the nucleus, the Stickyflare could affect the available sites for the spliceosome. This would lead to the ability to control cell differentiation or fate.

Detection

The present disclosure provides compositions and methods for quantifying and spatio-temporally tracking a target molecule. The target molecule, in various embodiments, is selected from the group consisting of an RNA molecule, a DNA molecule, a hybrid RNA:DNA molecule, or a polypeptide. The RNA molecule, in various embodiments, is messenger RNA (mRNA), pre-mRNA, micro-RNA (miRNA), or pri-miRNA. In further embodiments, the DNA or RNA target molecule is single stranded or double stranded. In embodiments in which the target molecule is a polypeptide, it is contemplated that the second polynucleotide is an aptamer.

Methods of detecting the SF include microscopy and flow cytometry. Flow cytometry for quantification-cells are treated with Stickyflares and allowed to interact with the cells for a time sufficient for the Stickyflares to be endocytosed, released into the cytoplasm, and interact with a sample population of the target molecule. In various aspects, this length of time changes depending on the target, cell type, and treatment conditions, but is contemplated to be from about 30 minutes to about 48 hours.

Microscopy for Quantification and Tracking: Treatment conditions are the same as those outlined above for flow cytometry. In the case of the flare containing a fluorescent marker, fluorescence microscopy may be used to track the reporter fluorophore. In other embodiments the flares are attached to something other than a fluorescent molecule. In such a case other techniques could be used such as scanning electron microscopy (SEM), transmission electron microscopy (TEM), and darkfield microscopy.

In some embodiments, the Stickyflare is used in vitro in cells and/or tissues that are fixed and permeabilized. In such embodiments, it is contemplated that the Stickyflare enters the cell and/or tissue and labels one or more nucleic acid targets.

Detectable Marker/Label

A "marker" as used herein is interchangeable with "label" and regardless of the type of interacting compound being identified, methods are provided wherein polynucleotide complex formation is detected by an observable change. In one aspect, complex formation gives rise to a change which is observed with a microscope, such as a fluorescent microscope.

It will be understood that a marker contemplated will include any of the fluorophores described herein as well as other detectable markers known in the art. For example, markers also include, but are not limited to, redox active probes, other nanoparticles, and quantum dots, as well as any marker which can be detected using spectroscopic means, i.e., those markers detectable using microscopy and cytometry.

Methods of Labeling Oligonucleotides

Methods of labeling oligonucleotides with fluorescent molecules and measuring fluorescence are well known in the art [see, e.g., Bartlett, Mol. Diag. Cancer 97: 77-87 (2004). Suitable fluorescent molecules are also well known in the art and include without limitation 1,8-ANS (1-Anilinonaphthalene-8-sulfonic acid), 1-Anilinonaphthalene-8-sulfonic acid (1,8-ANS), 5-(and-6)-Carboxy-2', 7'-dichlorofluorescein pH 9.0, 5-FAM pH 9.0, 5-ROX (5-Carboxy-X-rhodamine, triethylammonium salt), 5-ROX pH 7.0, 5-TAMRA, 5-TAMRA pH 7.0, 5-TAMRA-MeOH, 6 JOE, 6,8-Difluoro-7-hydroxy-4-methylcoumarin pH 9.0, 6-Carboxyrhodamine 6G pH 7.0, 6-Carboxyrhodamine 6G, hydrochloride, 6-HEX, SE pH 9.0, 6-TET, SE pH 9.0, 7-Amino-4-methylcoumarin pH 7.0, 7-Hydroxy-4-methylcoumarin, 7-Hydroxy-4-methylcoumarin pH 9.0, Alexa 350, Alexa 405, Alexa 430, Alexa 488, Alexa 532, Alexa 546, Alexa 555, Alexa 568, Alexa 594, Alexa 647, Alexa 660, Alexa 680, Alexa 700, Alexa Fluor 430 antibody conjugate pH 7.2, Alexa Fluor 488 antibody conjugate pH 8.0, Alexa Fluor 488 hydrazide-water, Alexa Fluor 532 antibody conjugate pH 7.2, Alexa Fluor 555 antibody conjugate pH 7.2, Alexa Fluor 568 antibody conjugate pH 7.2, Alexa Fluor 610 R-phycoerythrin streptavidin pH 7.2, Alexa Fluor 647 antibody conjugate pH 7.2, Alexa Fluor 647 R-phycoerythrin streptavidin pH 7.2, Alexa Fluor 660 antibody conjugate pH 7.2, Alexa Fluor 680 antibody conjugate pH 7.2, Alexa Fluor 700 antibody conjugate pH 7.2, Allophycocyanin pH 7.5, AMCA conjugate, Amino Coumarin, APC (allophycocyanin), Atto 647, BCECF pH 5.5, BCECF pH 9.0, BFP (Blue Fluorescent Protein), BO-PRO-1-DNA, BO-PRO-3-DNA, BOBO-1-DNA, BOBO-3-DNA, BODIPY 650/665-X, MeOH, BODIPY FL conjugate, BODIPY FL, MeOH, Bodipy R6G SE, BODIPY R6G, MeOH, BODIPY TMR-X antibody conjugate pH 7.2, Bodipy TMR-X conjugate, BODIPY TMR-X, MeOH, BODIPY TMR-X, SE, BODIPY TR-X phallacidin pH 7.0, BODIPY TR-X, MeOH, BODIPY TR-X, SE, BOPRO-1, BOPRO-3, Calcein, Calcein pH 9.0, Calcium Crimson, Calcium Crimson Ca2+, Calcium Green, Calcium Green-1 Ca2+, Calcium Orange, Calcium Orange Ca2+, Carboxynaphthofluorescein pH 10.0, Cascade Blue, Cascade Blue BSA pH 7.0, Cascade Yellow, Cascade Yellow antibody conjugate pH 8.0, CFDA, CFP (Cyan Fluorescent Protein), CI-NERF pH 2.5, CI-NERF pH 6.0, Citrine, Coumarin, Cy 2, Cy 3, Cy 3.5, Cy 5, Cy 5.5, CyQUANT GR-DNA, Dansyl Cadaverine, Dansyl Cadaverine, MeOH, DAPI, DAPI-DNA, Dapoxyl (2-aminoethyl) sulfonamide, DDAO pH 9.0, Di-8 ANEPPS, Di-8-ANEPPS-lipid, DiI, DiO, DM-NERF pH 4.0, DM-NERF pH 7.0, DsRed, DTAF, dTomato, eCFP (Enhanced Cyan Fluorescent Protein), eGFP (Enhanced Green Fluorescent Protein), Eosin, Eosin antibody conjugate pH 8.0, Erythrosin-5-isothiocyanate pH 9.0, Ethidium Bromide, Ethidium homodimer, Ethidium homodimer-1-DNA, eYFP (Enhanced Yellow Fluorescent Protein), FDA, FITC, FITC antibody conjugate pH 8.0, FlAsH, Fluo-3, Fluo-3 Ca2+, Fluo-4, Fluor-Ruby, Fluorescein, Fluorescein 0.1 M NaOH, Fluorescein antibody conjugate pH 8.0, Fluorescein dextran pH 8.0, Fluorescein pH 9.0, Fluoro-Emerald, FM 1-43, FM 1-43 lipid, FM 4-64, FM 4-64, 2% CHAPS, Fura Red Ca2+, Fura Red, high Ca, Fura Red, low Ca, Fura-2 Ca2+, Fura-2, high Ca, Fura-2, no Ca, GFP (S65T), HcRed, Hoechst 33258, Hoechst 33258-DNA, Hoechst 33342, Indo-1 Ca2+, Indo-1, Ca free, Indo-1, Ca saturated, JC-1, JC-1 pH 8.2, Lissamine rhodamine, LOLO-1-DNA, Lucifer Yellow, CH, LysoSensor Blue, LysoSensor Blue pH 5.0, LysoSensor Green, LysoSensor Green pH 5.0, LysoSensor Yellow pH 3.0, LysoSensor Yellow pH 9.0, LysoTracker Blue, LysoTracker Green, LysoTracker Red, Magnesium Green, Magnesium Green Mg2+, Magnesium Orange, Marina Blue, mBanana, mCherry, mHoneydew, MitoTracker Green, MitoTracker Green FM, MeOH, MitoTracker Orange, MitoTracker Orange, MeOH, MitoTracker Red, MitoTracker Red, MeOH, mOrange, mPlum, mRFP, mStrawberry, mTangerine, NBD-X, NBD-X, MeOH, NeuroTrace 500/525, green fluorescent Niss1 stain-RNA, Nile Blue, EtOH, Nile Red, Nile Red-lipid, Niss1, Oregon Green 488, Oregon Green 488 antibody conjugate pH 8.0, Oregon Green 514, Oregon Green 514 antibody conjugate pH 8.0, Pacific Blue, Pacific Blue antibody conjugate pH 8.0, Phycoerythrin, PicoGreen dsDNA quantitation reagent, PO-PRO-1, PO-PRO-1-DNA, PO-PRO-3, PO-PRO-3-DNA, POPO-1, POPO-1-DNA, POPO-3, Propidium Iodide, Propidium Iodide-DNA, R-Phycoerythrin pH 7.5, ReAsH, Resorufin, Resorufin pH 9.0, Rhod-2, Rhod-2 Ca2+, Rhodamine, Rhodamine 110, Rhodamine 110 pH 7.0, Rhodamine 123, MeOH, Rhodamine Green, Rhodamine phalloidin pH 7.0, Rhodamine Red-X antibody conjugate pH 8.0, Rhodaminen Green pH 7.0, Rhodol Green antibody conjugate pH 8.0, Sapphire, SBFI-Na+, Sodium Green Na+, Sulforhodamine 101, EtOH, SYBR Green I, SYPRO Ruby, SYTO 13-DNA, SYTO 45-DNA, SYTOX Blue-DNA, Tetramethylrhodamine antibody conjugate pH 8.0, Tetramethylrhodamine dextran pH 7.0, Texas Red-X antibody conjugate pH 7.2, TO-PRO-1-DNA, TO-PRO-3-DNA, TOTO-1-DNA, TOTO-3-DNA, TRITC, X-Rhod-1 Ca2+, YO-PRO-1-DNA, YO-PRO-3-DNA, YOYO-1-DNA, and YOYO-3-DNA.

In yet another embodiment, two types of fluorescent-labeled polynucleotides attached to two different SNAs can be used as long as the SNAs have the ability to quench the detectable marker being utilized. Suitable particles include polymeric particles (such as, without limitation, polystyrene particles, polyvinyl particles, acrylate and methacrylate particles), liposomal particles, glass particles, latex particles, Sepharose beads and others like particles well known in the art. Methods of attaching oligonucleotides to such particles are well known and routinely practiced in the art. See Chrisey et al., 1996, *Nucleic Acids Research*, 24: 3031-3039 (glass) and Charreyre et al., 1997 *Langmuir*, 13: 3103-3110, Fahy et al., 1993, *Nucleic Acids Research*, 21: 1819-1826, Elaissari et al., 1998, *J. Colloid Interface Sci.*, 202: 251-260, Kolarova et al., 1996, *Biotechniques*, 20: 196-198 and Wolf et al., 1987, *Nucleic Acids Research*, 15: 2911-2926 (polymer/latex).

Other labels besides fluorescent molecules can be used, such as chemiluminescent molecules, which will give a detectable signal or a change in detectable signal upon hybridization.

Polynucleotides

As used herein, the term "polynucleotide," either functionalized on a SNA or as a target molecule, is used interchangeably with the term oligonucleotide.

The term "nucleotide" or its plural as used herein is interchangeable with modified forms as discussed herein and otherwise known in the art. In certain instances, the art uses the term "nucleobase" which embraces naturally-occurring nucleotides as well as modifications of nucleotides that can be polymerized.

Methods of making polynucleotides of a predetermined sequence are well-known in the art. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically.

In various aspects, methods provided include use of polynucleotides which are DNA oligonucleotides, RNA oligonucleotides, or combinations of the two types. Modified forms of oligonucleotides are also contemplated which include those having at least one modified internucleotide linkage. Modified polynucleotides or oligonucleotides are described in detail herein below.

Spacers

In certain aspects, compositions are contemplated which include those wherein a nanoparticle comprises a polynucleotide which further comprises a spacer. In specific aspects, the first polynucleotide comprises a spacer.

"Spacer" as used herein means a moiety that serves to increase distance between the nanoparticle and the polynucleotide, or to increase distance between individual polynucleotides when attached to the nanoparticle in multiple copies. In aspects of the disclosure wherein a nanoparticle is used for a biological activity, it is contemplated that the spacer does not directly participate in the activity of the polynucleotide to which it is attached.

Thus, in some aspects, the spacer is contemplated herein as being located between individual polynucleotides in tandem, whether the polynucleotides have the same sequence or have different sequences. In one aspect, the spacer when present is an organic moiety. In another aspect, the spacer is a polymer, including but not limited to a water-soluble polymer, a nucleic acid, a polypeptide, an oligosaccharide, a carbohydrate, a lipid, or a combination thereof.

In instances wherein the spacer is a polynucleotide, the length of the spacer in various embodiments at least about 5 nucleotides, at least about 10 nucleotides, 10-30 nucleotides, or even greater than 30 nucleotides. In various aspects, the spacer may have any sequence which does not interfere with the ability of the polynucleotides to become bound to the nanoparticles or to the second polynucleotide. In certain aspects, the bases of the polynucleotide spacer are all adenines, all thymines, all cytidines, all guanines, all uracils, or all some other modified base.

Modified Oligonucleotides

Specific examples of oligonucleotides include those containing modified backbones or non-natural internucleoside linkages. Oligonucleotides having modified backbones include those that retain a phosphorus atom in the backbone and those that do not have a phosphorus atom in the backbone. Modified oligonucleotides that do not have a phosphorus atom in their internucleoside backbone are considered to be within the meaning of "oligonucleotide."

Modified oligonucleotide backbones containing a phosphorus atom include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Also contemplated are oligonucleotides having inverted polarity comprising a single 3' to 3' linkage at the 3'-most internucleotide linkage, i.e. a single inverted nucleoside residue which may be abasic (the nucleotide is missing or has a hydroxyl group in place thereof). Salts, mixed salts and free acid forms are also contemplated. Representative United States patents that teach the preparation of the above phosphorus-containing linkages include, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. See, for example, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, the disclosures of which are incorporated herein by reference in their entireties.

In still other embodiments, oligonucleotide mimetics wherein both one or more sugar and/or one or more internucleotide linkage of the nucleotide units are replaced with "non-naturally occurring" groups. In one aspect, this embodiment contemplates a peptide nucleic acid (PNA). In PNA compounds, the sugar-backbone of an oligonucleotide is replaced with an amide containing backbone. See, for example U.S. Pat. Nos. 5,539,082; 5,714,331; and 5,719,262, and Nielsen et al., 1991, *Science*, 254: 1497-1500, the disclosures of which are herein incorporated by reference.

In still other embodiments, oligonucleotides are provided with phosphorothioate backbones and oligonucleosides with heteroatom backbones, and including —$CH_2$—NH—O—$CH_2$—, —$CH_2$—N($CH_3$)—O—$CH_2$—, —$CH_2$—O—N($CH_3$)—$CH_2$—, —$CH_2$—N($CH_3$)—N($CH_3$)—$CH_2$— and —O—N($CH_3$)—$CH_2$—$CH_2$— described in U.S. Pat. Nos. 5,489,677, and 5,602,240. Also contemplated are oligonucleotides with morpholino backbone structures described in U.S. Pat. No. 5,034,506.

In various forms, the linkage between two successive monomers in the oligo consists of 2 to 4, desirably 3, groups/atoms selected from —CH$_2$—, —O—, —S—, —NR$^H$—, >C=O, >C=NR$^H$, >C=S, —Si(R")$_2$—, —SO—, —S(O)$_2$—, —P(O)$_2$—, —PO(BH$_3$)—, —P(O, S)—, —P(S)$_2$—, —PO(R")—, —PO(OCH$_3$)—, and —PO(NHR$^H$)—, where RH is selected from hydrogen and C$_{1-4}$-alkyl, and R" is selected from C$_{1-6}$-alkyl and phenyl. Illustrative examples of such linkages are —CH$_2$—CH$_2$—CH$_2$—, —CH$_2$—CO—CH$_2$—, —CH$_2$—CHOH—CH$_2$—, —O—CH$_2$—O—, —O—CH$_2$—CH$_2$—, —O—CH$_2$—CH= (including R$^5$ when used as a linkage to a succeeding monomer), —CH$_2$—CH$_2$—O—, —NR$^H$—CH$_2$—CH$_2$—, —CH$_2$—CH$_2$—NR$^H$—, —CH$_2$—NR$^H$—CH$_2$—, —O—CH$_2$—CH$_2$—NR$^H$—, —NR$^H$—CO—O—, —NR$^H$—CO—NR$^H$—, —NR$^H$—CS—NR$^H$—, —NR$^H$—C(=NR$^H$)—NR$^H$—, —NR$^H$—CO—CH$_2$—NR$^H$—O—CO—O—, —O—CO—CH$_2$—O—, —O—CH$_2$—CO—O—, —CH$_2$—CO—NR$^H$—, —O—CO—NR$^H$—, —NR$^H$—CO—CH$_2$—, —O—CH$_2$—CO—NR$^H$—, —O—CH$_2$—CH$_2$—NR$^H$—, —CH=N—O—, —CH$_2$—NR$^H$—O—, —CH$_2$—O—N= (including R$^5$ when used as a linkage to a succeeding monomer), —CH$_2$—O—NR$^H$—, —CO—NR$^H$—CH$_2$—, —CH$_2$—NR$^H$—, —CH$_2$—NR$^H$—CO—, —O—NR$^H$—CH$_2$—, —O—NR$^H$, —O—CH$_2$—S—, —S—CH$_2$—O—, —CH$_2$—CH$_2$—S—, —O—CH$_2$—CH$_2$—S—, —S—CH$_2$—CH= (including R$^5$ when used as a linkage to a succeeding monomer), —S—CH$_2$—CH$_2$—, —S—CH$_2$—CH$_2$—O—, —S—CH$_2$—CH$_2$—S—, —CH$_2$—S—CH$_2$—, —CH$_2$—SO—CH$_2$—, —CH$_2$—SO$_2$—CH$_2$—, —O—SO—O—, —O—S(O)$_2$—O—, —O—S(O)$_2$—CH$_2$—, —O—S(O)$_2$—NR$^H$—, —NR$^H$—S(O)$_2$—CH$_2$—; —O—S(O)$_2$—CH$_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —O—P(S)$_2$—S—, —S—P(O)$_2$—S—, —S—P(O,S)—S—, —S—P(S)$_2$—S—, —O—PO(R")—O—, —O—PO(OCH$_3$)—O—, —O—PO(OCH$_2$CH$_3$)—O—, —O—PO(OCH$_2$CH$_2$S—R)—O—, —O—PO(BH$_3$)—O—, —O—PO(NHR$^N$)—O—, —O—P(O)$_2$—NR$^H$H—, —NR$^H$—P(O)$_2$—O—, —O—P(O,NR$^H$)—O—, —CH$_2$—P(O)$_2$—O—, —O—P(O)$_2$—CH$_2$—, and —O—Si(R")$_2$—O—; among which —CH$_2$—CO—NR$^H$—, —CH$_2$—NR$^H$—O—, —S—CH$_2$—O—, —O—P(O)$_2$—O—, —O—P(-O,S)—O—, —O—P(S)$_2$—O—, —NR$^H$P(O)$_2$—O—, —O—P(O,NR$^H$)—O—, —O—PO(R")—O—, —O—PO(CH$_3$)—O—, and —O—PO(NHR$^N$)—O—, where RH is selected form hydrogen and C$_{1-4}$-alkyl, and R" is selected from C$_{1-6}$-alkyl and phenyl, are contemplated. Further illustrative examples are given in Mesmaeker et. al., 1995, *Current Opinion in Structural Biology*, 5: 343-355 and Susan M. Freier and Karl-Heinz Altmann, 1997, *Nucleic Acids Research*, vol 25: pp 4429-4443.

Still other modified forms of oligonucleotides are described in detail in U.S. Patent Application No. 20040219565, the disclosure of which is incorporated by reference herein in its entirety.

Modified oligonucleotides may also contain one or more substituted sugar moieties. In certain aspects, oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Other embodiments include O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$]$_2$, where n and m are from 1 to about 10. Other oligonucleotides comprise one of the following at the 2' position: C$_1$ to C$_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In one aspect, a modification includes 2'-methoxyethoxy (2'-O—CH$_2$CH$_2$OCH$_3$, also known as 2'-O-(2-methoxyethyl) or 2'-MOE) (Martin et al., 1995, *Helv. Chim. Acta*, 78: 486-504) i.e., an alkoxyalkoxy group. Other modifications include 2'-dimethylaminooxyethoxy, i.e., a O(CH$_2$)$_2$ON(CH$_3$)$_2$ group, also known as 2'-DMAOE, as described in examples herein below, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$, also described in examples herein below.

Still other modifications include 2'-methoxy (2'-O—CH$_3$), 2'-aminopropoxy (2'-OCH$_2$CH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. In one aspect, a 2'-arabino modification is 2'-F. Similar modifications may also be made at other positions on the oligonucleotide, for example, at the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. See, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, the disclosures of which are incorporated by reference in their entireties herein.

In one aspect, a modification of the sugar includes Locked Nucleic Acids (LNAs) in which the 2'-hydroxyl group is linked to the 3' or 4' carbon atom of the sugar ring, thereby forming a bicyclic sugar moiety. The linkage is in certain aspects is a methylene (—CH$_2$—)$_n$ group bridging the 2' oxygen atom and the 4' carbon atom wherein n is 1 or 2. LNAs and preparation thereof are described in WO 98/39352 and WO 99/14226.

Oligonucleotides may also include base modifications or substitutions. As used herein, "unmodified" or "natural" bases include the purine bases adenine (A) and guanine (G), and the pyrimidine bases thymine (T), cytosine (C) and uracil (U). Modified bases include other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,750,692 and 5,681,941, the disclosures of which are incorporated herein by reference.

A "modified base" or other similar term refers to a composition which can pair with a natural base (e.g., adenine, guanine, cytosine, uracil, and/or thymine) and/or can pair with a non-naturally occurring base. In certain aspects, the modified base provides a $T_m$ differential of 15, 12, 10, 8, 6, 4, or 2° C. or less. Exemplary modified bases are described in EP 1 072 679 and WO 97/12896.

By "nucleobase" is meant the naturally occurring nucleobases adenine (A), guanine (G), cytosine (C), thymine (T) and uracil (U) as well as non-naturally occurring nucleobases such as xanthine, diaminopurine, 8-oxo-$N^6$-methyladenine, 7-deazaxanthine, 7-deazaguanine, $N^4,N^4$-ethanocytosin, N',N'-ethano-2,6-diaminopurine, 5-methylcytosine (mC), 5-($C^3$-$C^6$)-alkynyl-cytosine, 5-fluorouracil, 5-bromouracil, pseudoisocytosine, 2-hydroxy-5-methyl-4-triazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" thus includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). The term "nucleosidic base" or "base unit" is further intended to include compounds such as heterocyclic compounds that can serve like nucleobases including certain "universal bases" that are not nucleosidic bases in the most classical sense but serve as nucleosidic bases. Especially mentioned as universal bases are 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Nanoparticles

As used herein, "nanoparticle" refers to small structures that are less than 10 µm, and preferably less than 5 µm, in any one dimension. In general, nanoparticles contemplated include any compound or substance with a high loading capacity for an oligonucleotide as described herein. A nanoparticle that is functionalized with one or more agents, such as a polynucleotide, is referred to herein as a Spherical Nucleic Acid (SNA).

Nanoparticles useful in the practice of the invention include metal (e.g., gold, silver, copper and platinum), semiconductor (e.g., CdSe, CdS, and CdS or CdSe coated with ZnS) and magnetic (e.g., ferromagnetite) colloidal materials, as long as the nanoparticle has the ability to quench the otherwise detectable marker. Other nanoparticles useful in the practice of the invention include ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs. The size of the nanoparticles is preferably from about 5 nm to about 150 nm (mean diameter), more preferably from about 5 to about 50 nm, most preferably from about 10 to about 30 nm. The size of the nanoparticle is contemplated to be from about 5 to about 10 nm, or about 5 to about 20 nm, or about 5 to about 30 nm, or about 5 to about 40 nm, or about 5 to about 60 nm, or about 5 to about 70 nm, or about 5 to about 80 nm, or about 5 to about 90 nm, or about 5 to about 100 nm, or about 5 to about 110 nm, or about 5 to about 120 nm, or about 5 to about 130 nm, or about 5 to about 140 nm, or about 10 to about 20 nm, or about 10 to about 40 nm, or about 10 to about 50 nm, or about 10 to about 60 nm, or about 10 to about 70 nm, or about 10 to about 80 nm, or about 10 to about 90 nm, or about 10 to about 100 nm, or about 10 to about 110 nm, or about 10 to about 120 nm, or about 10 to about 130 nm, or about 10 to about 140 nm, or about 10 to about 150 nm. The nanoparticles may also be rods, prisms, or tetrahedra.

Thus, nanoparticles are contemplated for use in the methods which comprise a variety of inorganic materials including, but not limited to, metals, semi-conductor materials or ceramics as described in U.S. Patent Application No. 20030147966. For example, metal-based nanoparticles include those described herein. Ceramic nanoparticle materials include, but are not limited to, brushite, tricalcium phosphate, alumina, silica, and zirconia. Organic materials from which nanoparticles are produced include carbon. Nanoparticle polymers include polystyrene, silicone rubber, polycarbonate, polyurethanes, polypropylenes, polymethylmethacrylate, polyvinyl chloride, polyesters, polyethers, and polyethylene. Biodegradable, biopolymer (e.g. polypeptides such as BSA, polysaccharides, etc.), other biological materials (e.g. carbohydrates), and/or polymeric compounds are also contemplated for use in producing nanoparticles.

In practice, methods are provided using any suitable nanoparticle having molecules attached thereto that are in general suitable for use in detection assays known in the art to the extent and do not interfere with polynucleotide complex formation, i.e., hybridization to form a double-strand or triple-strand complex. The size, shape and chemical composition of the particles contribute to the properties of the resulting oligonucleotide-functionalized nanoparticle. These properties include for example, optical properties, optoelectronic properties, electrochemical properties, electronic properties, stability in various solutions, magnetic properties, and pore and channel size variation. The use of mixtures of particles having different sizes, shapes and/or chemical compositions, as well as the use of nanoparticles having uniform sizes, shapes and chemical composition, is contemplated. Examples of suitable particles include, without limitation, nanoparticles, aggregate particles, isotropic (such as spherical particles) and anisotropic particles (such as non-spherical rods, tetrahedral, prisms) and core-shell particles such as the ones described in U.S. patent application Ser. No. 10/034,451, filed Dec. 28, 2002 and International application no. PCT/US01/50825, filed Dec. 28, 2002, the disclosures of which are incorporated by reference in their entirety.

Methods of making metal, semiconductor and magnetic nanoparticles are well-known in the art. See, for example, Schmid, G. (ed.) Clusters and Colloids (VCH, Weinheim, 1994); Hayat, M. A. (ed.) Colloidal Gold: Principles, Methods, and Applications (Academic Press, San Diego, 1991); Massart, R., IEEE Transactions On Magnetics, 17, 1247 (1981); Ahmadi, T. S. et al., *Science,* 272, 1924 (1996); Henglein, A. et al., *J. Phys. Chem.,* 99, 14129 (1995); Curtis, A. C. et al., *Angew. Chem. Int. Ed. Engl.,* 27, 1530 (1988). Preparation of polyalkylcyanoacrylate nanoparticles prepared is described in Fattal, et al., *J. Controlled Release* (1998) 53: 137-143 and U.S. Pat. No. 4,489,055. Methods for making nanoparticles comprising poly(D-glucaramidoamine)s are described in Liu, et al., *J. Am. Chem. Soc.* (2004) 126:7422-7423. Preparation of nanoparticles comprising polymerized methylmethacrylate (MMA) is described in Tondelli, et al., *Nucl. Acids Res.* (1998) 26:5425-5431, and preparation of dendrimer nanoparticles is described in, for example Kukowska-Latallo, et al., *Proc. Natl. Acad. Sci. USA* (1996) 93:4897-4902 (Starburst polyamidoamine dendrimers).

Suitable nanoparticles are also commercially available from, for example, Ted Pella, Inc. (gold), Amersham Corporation (gold) and Nanoprobes, Inc. (gold).

Also as described in U.S. Patent Application No 20030147966, nanoparticles comprising materials described herein are available commercially or they can be produced from progressive nucleation in solution (e.g., by colloid reaction), or by various physical and chemical vapor deposition processes, such as sputter deposition. See, e.g., HaVashi, (1987) Vac. Sci. Technol. July/August 1987, A5(4):1375-84; Hayashi, (1987) Physics Today, December 1987, pp. 44-60; MRS Bulletin, January 1990, pgs. 16-47.

As further described in U.S. Patent Application No. 20030147966, nanoparticles contemplated are produced using HAuCl$_4$ and a citrate-reducing agent, using methods known in the art. See, e.g., Marinakos et al., (1999) *Adv. Mater.* 11: 34-37; Marinakos et al., (1998) *Chem. Mater.* 10: 1214-19; Enustun & Turkevich, (1963) *J. Am. Chem. Soc.* 85: 3317. Tin oxide nanoparticles having a dispersed aggregate particle size of about 140 nm are available commercially from Vacuum Metallurgical Co., Ltd. of Chiba, Japan. Other commercially available nanoparticles of various compositions and size ranges are available, for example, from Vector Laboratories, Inc. of Burlingame, Calif.

Regulatory Polynucleotides

As disclosed herein, a Stickyflare comprises a first polynucleotide and a second polynucleotide, each as described herein. The Stickyflare, in various aspects, further comprises a regulatory polynucleotide. The regulatory polynucleotide, in various embodiments, is DNA or RNA. For example and without limitation, the regulatory polynucleotide is selected from the group consisting of an antisense polynucleotide, short interfering RNA (siRNA), piRNA, or microRNA (miRNA).

Compositions and methods are therefore contemplated wherein the regulatory polynucleotide is about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, and all polynucleotides intermediate in length of the sizes specifically disclosed to the extent that the regulatory polynucleotide is able to achieve the desired result. Accordingly, polynucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 nucleotides in length are contemplated for the regulatory polynucleotide.

Methods for inhibiting gene product expression provided include those wherein expression of the target gene product is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or 100% compared to gene product expression in the absence of an SNA of the disclosure. In other words, methods provided embrace those which results in essentially any degree of inhibition of expression of a target gene product.

The degree of inhibition is determined in vivo from a body fluid sample or from a biopsy sample or by imaging techniques well known in the art. Alternatively, the degree of inhibition is determined in a cell culture assay, generally as a predictable measure of a degree of inhibition that can be expected in vivo resulting from use of a specific type of nanoparticle and a specific polynucleotide.

Attaching Polynucleotides to Nanoparticles

The nanoparticles, the polynucleotides or both are functionalized in order to attach the oligonucleotides to the nanoparticles. Such methods are known in the art. For instance, oligonucleotides functionalized with alkanethiols at their 3'-termini or 5'-termini readily attach to gold nanoparticles. See Whitesides, 1995, Proceedings of the Robert A. Welch Foundation 39th Conference On Chemical Research Nanophase Chemistry, Houston, Tex., pages 109-121. See also, Mucic et al., 1996, *Chem. Commun.* 555-557 (describes a method of attaching 3' thiol DNA to flat gold surfaces; this method can be used to attach oligonucleotides to nanoparticles). The alkanethiol method can also be used to attach oligonucleotides to other metal, semiconductor and magnetic colloids and to the other nanoparticles listed above. Other functional groups for attaching oligonucleotides to solid surfaces include phosphorothioate groups (see, e.g., U.S. Pat. No. 5,472,881 for the binding of oligonucleotide-phosphorothioates to gold surfaces), substituted alkylsiloxanes (see, e.g. Burwell, 1974, *Chemical Technology*, 4: 370-377 and Matteucci and Caruthers, 1981, *J. Am. Chem. Soc.*, 103: 3185-3191 for binding of oligonucleotides to silica and glass surfaces, and Grabar et al., 1995, *Anal. Chem.*, 67: 735-743 for binding of aminoalkylsiloxanes and for similar binding of mercaptoaklylsiloxanes). Oligonucleotides terminated with a 5' thionucleoside or a 3' thionucleoside may also be used for attaching oligonucleotides to solid surfaces. The following references describe other methods which may be employed to attach oligonucleotides to nanoparticles: Nuzzo et al., 1987, *J. Am. Chem. Soc.*, 109: 2358 (disulfides on gold); Allara and Nuzzo, 1985, *Langmuir*, 1: 45 (carboxylic acids on aluminum); Allara and Tompkins, 1974, *J. Colloid Interface Sci.*, 49: 410-421 (carboxylic acids on copper); Iler, The Chemistry Of Silica, Chapter 6, (Wiley 1979) (carboxylic acids on silica); Timmons and Zisman, 1965, *J. Phys. Chem.*, 69: 984-990 (carboxylic acids on platinum); Soriaga and Hubbard, 1982, *J. Am. Chem. Soc.*, 104: 3937 (aromatic ring compounds on platinum); Hubbard, 1980, *Acc. Chem. Res.*, 13: 177 (sulfolanes, sulfoxides and other functionalized solvents on platinum); Hickman et al., 1989, *J. Am. Chem. Soc.*, 111: 7271 (isonitriles on platinum); Maoz and Sagiv, 1987, *Langmuir*, 3: 1045 (silanes on silica); Maoz and Sagiv, 1987, *Langmuir*, 3: 1034 (silanes on silica); Wasserman et al., 1989, *Langmuir*, 5: 1074 (silanes on silica); Eltekova and Eltekov, 1987, *Langmuir*, 3: 951 (aromatic carboxylic acids, aldehydes, alcohols and methoxy groups on titanium dioxide and silica); Lec et al., 1988, *J. Phys. Chem.*, 92: 2597 (rigid phosphates on metals). Additionally, any suitable method for attaching oligonucleotides onto the nanoparticle surface may be used. A particularly preferred method for attaching oligonucleotides onto a surface is based on an aging process described in U.S. patent application Ser. No. 09/344,667, filed Jun. 25, 1999; application Ser. No. 09/603,830, filed Jun. 26, 2000; application Ser. No. 09/760,500, filed Jan. 12, 2001; application Ser. No. 09/820,279, filed Mar. 28, 2001; application Ser. No. 09/927,777, filed Aug. 10, 2001; and in International application nos. PCT/US97/12783, filed Jul. 21, 1997; PCT/US00/17507, filed Jun. 26, 2000; PCT/US01/01190, filed Jan. 12, 2001; PCT/US01/10071, filed Mar. 28, 2001, the disclosures which are incorporated by reference in their entirety. The aging process provides nanoparticle-oligonucleotide conjugates with unexpected enhanced stability and selectivity. The method comprises providing oligonucleotides preferably having covalently bound thereto a moiety comprising a functional group which can bind to the nanoparticles. The moieties and functional groups are those that allow for binding (i.e., by chemisorption or covalent bonding) of the oligonucleotides to nanoparticles. For instance, oligonucleotides having an alkanethiol, an alkanedisulfide or a cyclic disulfide covalently bound to their 5' or 3' ends can be used to bind the oligonucleotides to a variety of nanoparticles, including gold nanoparticles.

The oligonucleotides are contacted with the nanoparticles in water for a time sufficient to allow at least some of the oligonucleotides to bind to the nanoparticles by means of the functional groups. Such times can be determined empirically. For instance, it has been found that a time of about 12-24 hours gives good results. Other suitable conditions for binding of the oligonucleotides can also be determined empirically. For instance, a concentration of about 10-20 nM nanoparticles and incubation at room temperature gives good results.

Next, at least one salt is added to the water to form a salt solution. The salt can be any suitable water-soluble salt. For instance, the salt may be sodium chloride, magnesium chloride, potassium chloride, ammonium chloride, sodium acetate, ammonium acetate, a combination of two or more of these salts, or one of these salts in phosphate buffer. Preferably, the salt is added as a concentrated solution, but it could be added as a solid. The salt can be added to the water all at one time or the salt is added gradually over time. By "gradually over time" is meant that the salt is added in at least two portions at intervals spaced apart by a period of time. Suitable time intervals can be determined empirically.

The ionic strength of the salt solution must be sufficient to overcome at least partially the electrostatic repulsion of the oligonucleotides from each other and, either the electrostatic attraction of the negatively-charged oligonucleotides for positively-charged nanoparticles, or the electrostatic repulsion of the negatively-charged oligonucleotides from negatively-charged nanoparticles. Gradually reducing the electrostatic attraction and repulsion by adding the salt gradually over time has been found to give the highest surface density of oligonucleotides on the nanoparticles. Suitable ionic strengths can be determined empirically for each salt or combination of salts. A final concentration of sodium chloride of from about 0.1 M to about 1.0 M in phosphate buffer, preferably with the concentration of sodium chloride being increased gradually over time, has been found to give good results.

After adding the salt, the oligonucleotides and nanoparticles are incubated in the salt solution for an additional period of time sufficient to allow sufficient additional oligonucleotides to bind to the nanoparticles to produce the stable nanoparticle-oligonucleotide conjugates. As will be described in detail below, an increased surface density of the oligonucleotides on the nanoparticles has been found to stabilize the conjugates. The time of this incubation can be determined empirically. A total incubation time of about 24-48, preferably 40 hours, has been found to give good results (this is the total time of incubation; as noted above, the salt concentration can be increased gradually over this total time). This second period of incubation in the salt solution is referred to herein as the "aging" step. Other suitable conditions for this "aging" step can also be determined empirically. For instance, incubation at room temperature and pH 7.0 gives good results.

The conjugates produced by use of the "aging" step have been found to be considerably more stable than those produced without the "aging" step. As noted above, this increased stability is due to the increased density of the oligonucleotides on the surfaces of the nanoparticles which is achieved by the "aging" step. An alternative "fast salt aging" process produced particles with comparable DNA densities and stability. By performing the salt additions in the presence of a surfactant, for example approximately 0.01% sodium dodecylsulfate (SDS), Tween, or polyethylene glycol (PEG), the salt aging process can be performed in about an hour.

The surface density achieved by the "aging" step will depend on the size and type of nanoparticles and on the length, sequence and concentration of the oligonucleotides. A surface density adequate to make the nanoparticles stable and the conditions necessary to obtain it for a desired combination of nanoparticles and oligonucleotides can be determined empirically. Generally, a surface density of at least 10 picomoles/cm$^2$ will be adequate to provide stable nanoparticle-oligonucleotide conjugates. Preferably, the surface density is at least 15 picomoles/cm$^2$. Since the ability of the oligonucleotides of the conjugates to hybridize with nucleic acid and oligonucleotide targets can be diminished if the surface density is too great, the surface density is preferably no greater than about 35-40 picomoles/cm$^2$. Compositions and methods are also provided wherein the oligonucleotide is bound to the nanoparticle at a surface density of at least 2 pmol/cm$^2$, at least 5 pmol/cm$^2$, at least 10 pmol/cm$^2$, at least 15 pmol/cm$^2$, at least 20 pmol/cm$^2$, at least 25 pmol/cm$^2$, at least 30 pmol/cm$^2$, at least 35 pmol/cm$^2$, at least 40 pmol/cm$^2$, at least 45 pmol/cm$^2$, at least 50 pmol/cm$^2$, or 50 pmol/cm$^2$ or more.

"Hybridization," which is used interchangeably with the term "complex formation" herein, means an interaction between two or three strands of nucleic acids by hydrogen bonds in accordance with the rules of Watson-Crick DNA complementarity, Hoogstein binding, or other sequence-specific binding known in the art. Alternatively it can mean an interaction between polypeptides as defined herein in accordance with sequence-specific binding properties known in the art. Hybridization can be performed under different stringency conditions known in the art. Under appropriate stringency conditions, hybridization between the two complementary strands or two polypeptides could reach about 60% or above, about 70% or above, about 80% or above, about 90% or above, about 95% or above, about 96% or above, about 97% or above, about 98% or above, or about 99% or above in the reactions.

In various aspects, the methods include use of two or three oligonucleotides which are 100% complementary to each other, i.e., a perfect match, while in other aspects, the individual oligonucleotides are at least (meaning greater than or equal to) about 95% complementary to each over the all or part of length of each oligonucleotide, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20% complementary to each other.

It is understood in the art that the sequence of the oligonucleotide used in the methods need not be 100% complementary to each other to be specifically hybridizable. Moreover, oligonucleotide may hybridize to each other over one or more segments such that intervening or adjacent segments are not involved in the hybridization event (e.g., a loop structure or hairpin structure). Percent complementarity between any given oligonucleotide can be determined routinely using BLAST programs (Basic Local Alignment Search Tools) and PowerBLAST programs known in the art (Altschul et al., 1990, *J. Mol. Biol.*, 215: 403-410; Zhang and Madden, 1997, *Genome Res.*, 7: 649-656).

In one aspect, methods are provided wherein the packing density of the oligonucleotides on the surface of the nanoparticle is sufficient to result in cooperative behavior between nanoparticles and between polynucleotide strands on a single nanoparticle. In another aspect, the cooperative behavior between the nanoparticles increases the resistance of the oligonucleotide to degradation.

As used herein, "stable" means that, for a period of at least six months after the conjugates are made, a majority of the oligonucleotides remain attached to the nanoparticles and the oligonucleotides are able to hybridize with nucleic acid and oligonucleotide targets under standard conditions encountered in methods of detecting nucleic acid and methods of nanofabrication.

In one aspect, methods are provided wherein each nanoparticle is functionalized with identical oligonucleotides, i.e., each oligonucleotide attached to the nanoparticle has the same length and the same sequence. In other aspects, each nanoparticle is functionalized with two or more oligonucleotides which are not identical, i.e., at least one of the attached oligonucleotides differ from at least one other attached oligonucleotide in that it has a different length and/or a different sequence.

The term "oligonucleotide" or "polynucleotide" includes those wherein a single sequence is attached to a nanoparticle, or multiple copies of the single sequence are attached. For example, in various aspects, an oligonucleotide is present in multiple copies in tandem, for example, two, three, four, five, six, seven eight, nine, ten or more tandem repeats.

All publications, patents and patent applications cited in this specification are herein incorporated by reference as if each individual publication or patent application were specifically and individually indicated to be incorporated by reference. In addition, the entire document is intended to be related as a unified disclosure, and it should be understood that all combinations of features described herein are contemplated, even if the combination of features are not found together in the same sentence, or paragraph, or section of this document. With respect to elements described as one or more members of a set, it should be understood that all combinations within the set are contemplated. The invention will be more fully understood by reference to the following examples which detail exemplary embodiments of the invention. They should not, however, be construed as limiting the scope of the invention.

Therapeutic Agents

"Therapeutic agent" as used herein means any compound useful for therapeutic or diagnostic purposes. The terms as used herein are understood to mean any compound that is administered to a patient for the treatment of a condition that can traverse a cell membrane more efficiently when attached to a nanoparticle of the disclosure than when administered in the absence of a nanoparticle of the disclosure. Therapeutic agents useful in the methods of the disclosure include those described in U.S. Patent Application Publication 2012/0282186, which is incorporated by reference herein in its entirety.

The present disclosure is applicable to any therapeutic agent for which delivery is desired. Non-limiting examples of such active agents as well as hydrophobic drugs are found in U.S. Pat. No. 7,611,728, which is incorporated by reference herein in its entirety.

Compositions and methods disclosed herein, in various embodiments, are provided wherein the nanoparticle comprises a multiplicity of therapeutic agents. In one aspect, compositions and methods are provided wherein the multiplicity of therapeutic agents are specifically attached to one nanoparticle. In another aspect, the multiplicity of therapeutic agents is specifically attached to more than one nanoparticle.

Therapeutic agents useful in the materials and methods of the present disclosure can be determined by one of ordinary skill in the art. Therapeutic agents include but are not limited to hydrophilic and hydrophobic compounds.

Protein therapeutic agents include, without limitation peptides, enzymes, structural proteins, receptors and other cellular or circulating proteins as well as fragments and derivatives thereof, the aberrant expression of which gives rise to one or more disorders. Therapeutic agents also include, as one specific embodiment, chemotherapeutic agents. Therapeutic agents also include, in various embodiments, a radioactive material.

EXAMPLES

The examples below show in exemplary embodiments how mRNA is quantified or tracked. It will be readily apparent that the specific mRNA used in the examples can be applied to any mRNA of interest, and that the specific mRNA is merely a representative to showcase the methods.

Example 1

Design of the SNAs of the Disclosure

The design of the Nanoflare necessarily does not allow for investigation of the spatial distribution of targeted RNA. Release of the flare through Nanoflare-transcript binding results in a displacement of the fluorophore from the nanoparticle construct, and thus the transcript, as the RNA remains bound to the antisense capture sequences of the Nanoflare. However, were the complementarity of the Nanoflare oligonucleotides reversed, the result would be a Nanoflare-like construct with the important difference that the flare strands themselves are complementary to, and potentially capable of binding RNA targets. Such a construct may be engineered to perform similarly to the Nanoflare, using base-pair recognition of a target to displace fluorescent flare strands quantifiably, with the additional benefit that the complementary flare remains bound to the RNA (FIG. 1). Herein we report the development of such a construct, termed the Stickyflare, and investigate its use as a platform for RNA quantification and real-time tracking of transcripts as they are transported within live cells.

Example 2

Stickyflare Synthesis

Oligonucleotides were synthesized using standard solid-phase phosphoramidite chemistry (Expedite 8909 Nucleotide Synthesis System (ABI)). All reagents were purchased from Glen Research. Oligonucleotides were purified by reverse-phase high performance liquid chromatography (HPLC). The oligonucleotide sequences used in this study are shown below.

| Description | Sequence (5'→3') | SEQ ID NO |
|---|---|---|
| Non-Targeting | CGT CTA CCT TCG CGC AAA AAA A-Alkane Thiol | 1 |
| Non-Targeting Flare | Cy5- GCG CGA AGG TAG GCG GAG TCG GTC GA | 2 |
| β-Actin | CCG GCA TGT GCA A AAA AAA A-Alkane Thiol | 3 |
| β-Actin Flare | Cy5- TTG CAC ATG CCG GAG CCG TTG TCG ACG A | 4 |
| β-Actin Target | TCGTCGACAACGGCTCCGGCATGTGCAA | 5 |

To make the DNA-functionalized SNA conjugates, alkylthiol-terminated actin and survivin oligonucleotides (3 µM each) were combined with citrate-capped 13 nm gold particles (13 nM) and incubated for 1 hour at room temperature. Next, phosphate buffer (pH=7.4), and sodium chloride were added to a final concentration of 5 mM, and 150 mM, respectively, and incubated overnight. Then, sodium chloride (NaCl) was added in 0.05M increments over three hours to achieve a final NaCl concentration of 300 mM, and the particles were stored at room temperature for four hours. Finally, the conjugates were purified by centrifugation and redispersed in Phosphate Buffered Saline (PBS).

Flares were hybridized on the purified DNA-gold nanoparticles (DNA-Au NPs) by adding a stoichiometric equivalent of 10 flares/nanoparticle. The solution was then heated to 65° C. and slowly cooled to room temperature overnight to facilitate hybridization. The resulting Stickyflares were then sterilized using a 0.2 µm acetate syringe filter (GE Healthcare) to prevent cell contamination and stored at 4° C.

Cell Culture and Stickyflare Treatment

HeLa cells were cultured in Dulbecco's Modified Eagle's Medium (FBS) (Gibco) supplemented with 10% Fetal Bovine Serum and 1% penicillin/streptomycin. Gene knockdown was performed by treating with 50 nM anti-actin siRNA (Santa Cruz Biotechnology) for 24 hours with RNAiMAX according to recommended protocol. Cells were then washed once with PBS and further cultured in supplemented OptiMEM. Stickyflare treatment was then performed at 400 pM Stickyflares for an additional 24 hours. Fluorescence of trypsinized cells was quantified by using a Guava Easycyte HT flow cytometer (Millipore). Confocal microscopy was performed with Zeiss 510 (Zeiss) and SP5 (Leica) confocal microscopes. Mitochondria were stained using CellLight® Mitochondria-GFP (Life technologies).

Evaluation of Target Recognition by Stickyflares

Figure 2:
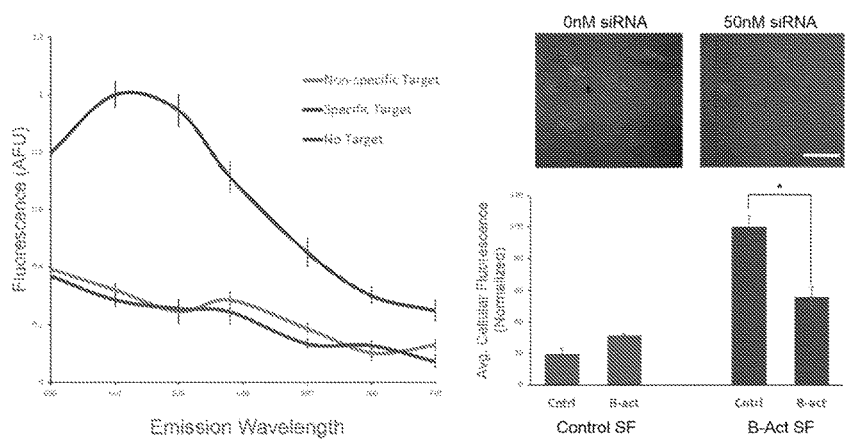
FIG. 2 depicts a characterization of Stickyflare target recognition and quantification. Left: In vitro assay demonstrating the sequence-specific release of fluorescent flares. Right: Representative confocal images of HeLa cells treated with β-actin Stickyflares and vehicle only (left), and 50 nM siRNA (right). Right graph: Flow cytometry quantification of β-actin knockdown using Stickyflares. "Cntrl" refers to treatment with vehicle alone; "B-act" indicates 50 nM siRNA treatment with β-actin siRNA. *p<0.001

Stickyflares were first evaluated in vitro for their ability to detect complementary nucleic acid targets. One nanomolar (nM) solutions of β-actin targeting Stickyflares were evaluated before and after the addition of fully-complementary targets in PBS. Upon addition of a complementary target, a significant increase in fluorescence was observed, indicating displacement of the fluorophore from the nanoparticle surface, while a non-complementary target had no measurable effect (FIG. 2a). Next, β-actin Stickyflares were evaluated in a cell culture model by flow cytometry. HeLa human cervical cancer cells were treated with 50 nM of either control or β-actin siRNA for 24 hours, after which the media was replaced with Stickyflare-containing media. After a further 18 hour incubation the fluorescence of each cell was quantified. β-actin Stickyflares detected a knockdown of mRNA expression levels compared to cells treated with control siRNA, while non-targeting control Stickyflares showed no significant difference (FIG. 2b). To further verify that the decreased fluorescence response was due to specific knockdown of β-actin, this experiment was repeated using β-actin targeting Smartflares (Millipore), a nanoflare construct capable of quantifying relative RNA expression.

Intracellular RNA Tracking by Stickyflares

The ability of Stickyflares to track the spatial distribution of RNA was evaluated using confocal microscopy. Two genes with disparate intracellular function and localization patterns were chosen to analyze spatial distribution within cells: β-actin mRNA and U1 small nuclear RNA (snRNA). In previous reports, B-actin mRNA has been found to localize at the growth cones of lamellae in embryonic fibroblasts. In contrast, U1 snRNA is imported into the nucleus, where it acts as a key component of the spliceosome.

Figure 3:
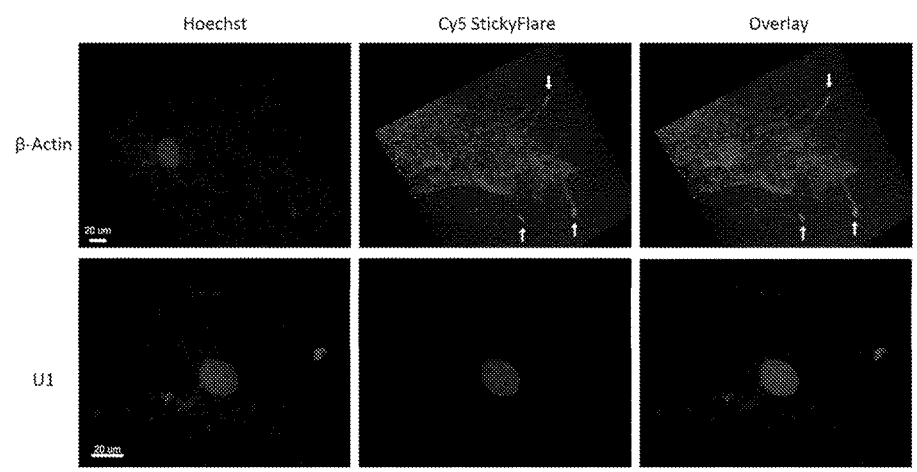
FIG. 3 shows RNA localization in Mouse Embryonic Fibroblasts. β-actin-targeting Stickyflares localize to the growth cone of growing lamellae (arrows in the upper middle and left panels), where β-actin RNA is found. In contrast, Stickyflares targeting the U1 nuclear RNA localize to the nucleus. Left panels: nuclear stain, middle panels: Stickyflares, right panels: overlay of nuclear stain and stickyflare.

MEFs were cultured in glass-bottomed cell culture chambers with Stickyflares for 12 hours, after which the cells were treated with a nuclear stain (Hoechst) for 10 minutes and imaged live. Fluorescence from cells treated with β-actin Stickyflares exhibited punctuate fluorescence throughout the cell body, and a demonstrable preference for the growth cone region of lamellae extensions (FIG. 3, top row). Additional highly fluorescent regions were seen within the lamellae extensions, marking β-actin RNA being actively transported to and from the growth cone. This active transport is further analyzed below. Importantly, Stickyflares are not limited to use in live cells, and verifying RNA localization in fixed cells is a convenient control. Therefore, fixed and permeabilized MEFs were treated with Stickyflares, confirming the growth cone specific localization observed in live cells. In contrast, MEFs treated with Stickyflares targeting U1 snRNA showed distinctly inter-nuclear fluorescence (FIG. 3, bottom row). Importantly, SNA constructs themselves are sequestered to the cytosol, and cannot enter the nucleus on their own. Thus, the nuclear localized fluorescence of U1 Stickyflares indicates specific release from the nanoparticle surface and subsequent transport into the nucleus.

Figure 4:
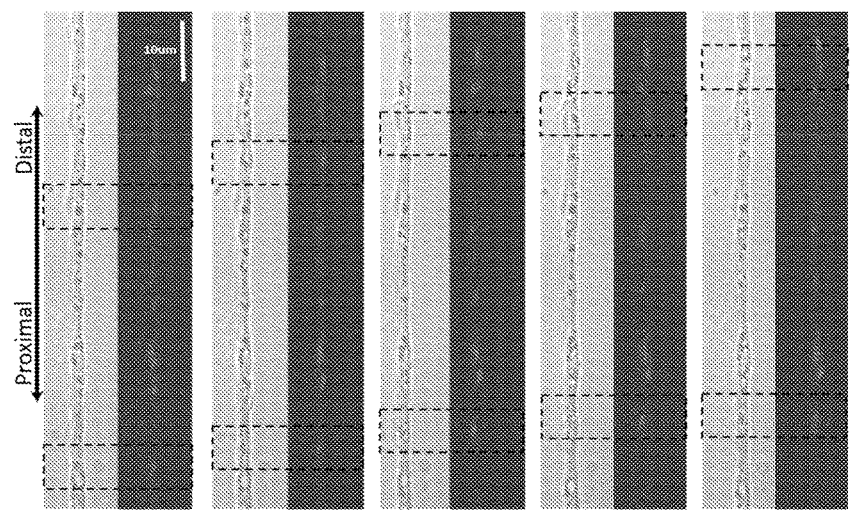
FIG. 4 depicts dynamic β-Actin mRNA transport in MEF cells. Endogenously expressed β-Actin mRNA is transported distally towards the growth cone. Dashed boxes indicate the labeled RNA being tracked. Each panel indicates a 50 second advancement and consists of a bright field and a fluorescent image. Cy5-labeled Stickyflare appear as bright spots in the fluorescent images.

Beyond studying the final localization of mRNA strands, the facile, non-invasive nature of the Stickyflare allows for real-time observation of dynamic RNA translocation in live cells. To demonstrate this, MEFs treated with β-actin Stickyflares were imaged every 10 seconds with a confocal microscope for a total of 10 minutes. When the plane of imaging was focused on lamellae, transport of β-actin mRNA was observed primarily (but not exclusively) in the distal direction towards the growth cone (FIG. 4). Furthermore, when focused directly at the body of the cell, RNA dynamics become even more evident, with hundreds of fluorescently-labeled β-actin sequences being transported throughout the cell.

Figure 5:
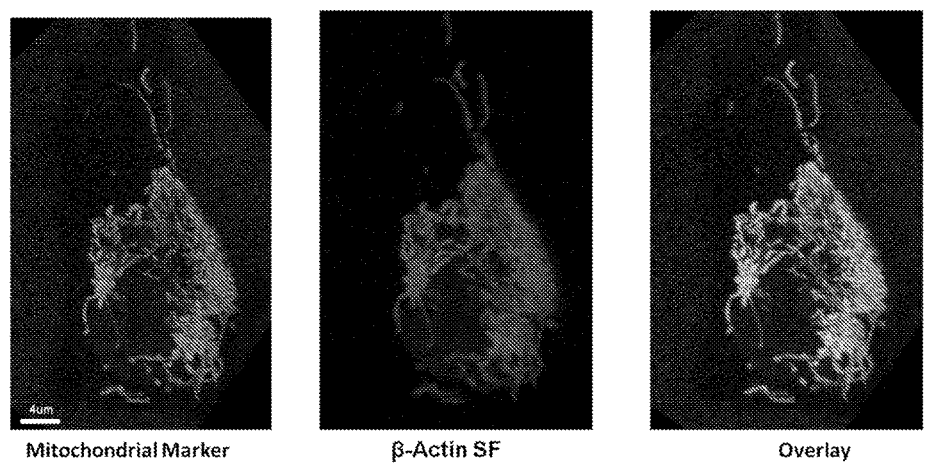
FIG. 5 shows that β-Actin mRNA colocalized with mitochondria in HeLa cells.

Similar analyses were performed in HeLa cells. In this case β-actin Stickyflares demonstrated a starkly different intracellular distribution, showing a high degree of colocalization with mitochondria (FIG. 5, right panel). In order to observe dynamic RNA movement, fluorescence was monitored in HeLa cells starved by culturing in Eagle's Balanced Salt Solution. Upon starvation, mitochondria and RNA both migrated towards the perinuclear region together, forming a more punctuate expression pattern, and maintaining colocalization.

Conclusion. The Stickyflare utilizes a targeting strategy that allows for targeting and quantifying RNA targets in live cells, and additionally exploits that recognition event to label target polynucleotides, enabling further analysis of, e.g., RNA transport and localization. As such, this SNA enables a complete analysis of target polynucleotide function in live cells from a single platform, and overcomes many limitations of previous analytical techniques. It is contemplated that the Stickyflare is a valuable tool for investigating, for example and without limitation, proper RNA function and its misregulation in disease, and make such studies accessible to a broader community given the ease of its application in cell culture. Further, the Stickyflare improves analyses in other model systems where asymmetric RNA expression is an essential component, such as, e.g., embryonic development, tissue and organ regeneration, and neurobiology.

Example 3

Additional Stickyflare Studies

Stickyflare Synthesis was as described in Example 2. Briefly, oligonucleotides were synthesized using standard solid-phase phosphoramidite chemistry (Expedite 8909 Nucleotide Synthesis System (ABI)). All reagents were purchased from Glen Research, and the oligonucleotides were purified by reverse-phase high performance liquid chromatography (HPLC). The oligonucleotide sequences used in this study are shown below.

| Description | Sequence (5'→3') | SEQ ID NO |
|---|---|---|
| Non-Targeting Thiol | CGT CTA CCT TCG CGC AAA AAA A-Alkane Thiol | 6 |
| Non-Targeting Flare | Cy5- GCG CGA AGG TAG GCG GAG TCG GTC GA | 7 |
| Survivin Thiol | GCA GCC CTT TCT CAA G AAA AAA A-Alkane Thiol | 8 |
| Survivin Flare | Cy5- CTT GAG AAA GGG CTG CCA GGC AGG GG | 9 |
| Survivin Target | CCC CTG CCT GGC AGC CCT TTC TCA AG | 10 |
| KRAS Thiol | GCC CTG TGT GAA CCT AAA AAA A-Alkane Thiol | 11 |
| KRAS Flare | Cy5- AGG TTC ACA CAG GGC CTG GCC TTG C | 12 |
| KRAS Target | G CAA GGC CAG GCC CTG TGT GAA CCT | 13 |
| β-Actin Thiol | CCG GCA TGT GCA A AAA AAA A-Alkane Thiol | 14 |
| β-Actin Flare | Cy5- TTG CAC ATG CCG GAG CCG TTG TCG ACG A | 15 |
| β-Actin Target | TCGTCGACAACGGCTCCGGCATGTGCAA | 16 |

To make the DNA-functionalized SNA-Au NP conjugates, alkylthiol-terminated actin and survivin oligonucleotides (3 μM each) were combined with citrate-capped 13 nm gold particles (13 nM) and incubated for 1 hour at room temperature. Next, phosphate buffer (pH=7.4) and sodium chloride were added to a final concentration 5 mM, and 150 mM, respectively, and incubated overnight. Next, sodium chloride was added to achieve a final concentration of 300 mM, and the particles were stored for four hours. Finally, the conjugates were purified by centrifugation and redispersed in Phosphate Buffer Solution (PBS).

Flares were hybridized on the purified DNA-Au NPs by adding 100 nM (10 flares/NP). The solution was then heated to 65° C. and slowly cooled to room temperature over four hours to allow hybridization. The resulting nanoflares were then sterilized using a 0.2 μm acetate syringe filter (GE Healthcare) to prevent cell contamination and stored at 4° C.

Cell Culture and Stickyflare Treatment

HeLa cells were cultured in Dulbecco's Modified Eagle's Medium (FBS) (Gibco) supplemented with 10% Fetal Bovine Serum and 1% penicillin/streptomycin. Gene knockdown was performed by treating with 50 nM anti-survivin siRNA (Santa Cruz Biotechnology) for 24 hours in opti-MEM according to recommended protocol. Cells were then washed once with PBS and further cultured in supplemented DMEM. SF treatment was then performed at 400 pM SFs for an additional 24 hours. Fluorescence of trypsinized cells was quantified by using a Guava Easycyte HT flow cytometer (Millipore). Confocal microscopy was performed with Zeiss 510 (Zeiss) and SP5 (Leica) confocal microscopes. Mitochondria were stained using CellLight® Mitochondria-GFP (Life technologies).

Results. Sticky Flares (SFs) were synthesized by attaching alkane-thiol terminated DNA to 13 nm gold nanoparticles. SFs targeting the anti-apoptotic oncogene survivin were made, due to its importance in cancer development and drug resistance. Alkane-thiol terminated oligonucleotides containing the target survivin sequence were immobilized on the nanoparticle using the methods described above. Following this, Flares complementary to survivin mRNA were hybridized to the alkane-thiol terminated DNA via complementary base pairing (FIG. 1). Ten flares per particle were hybridized to the SNA.

Figure 6:
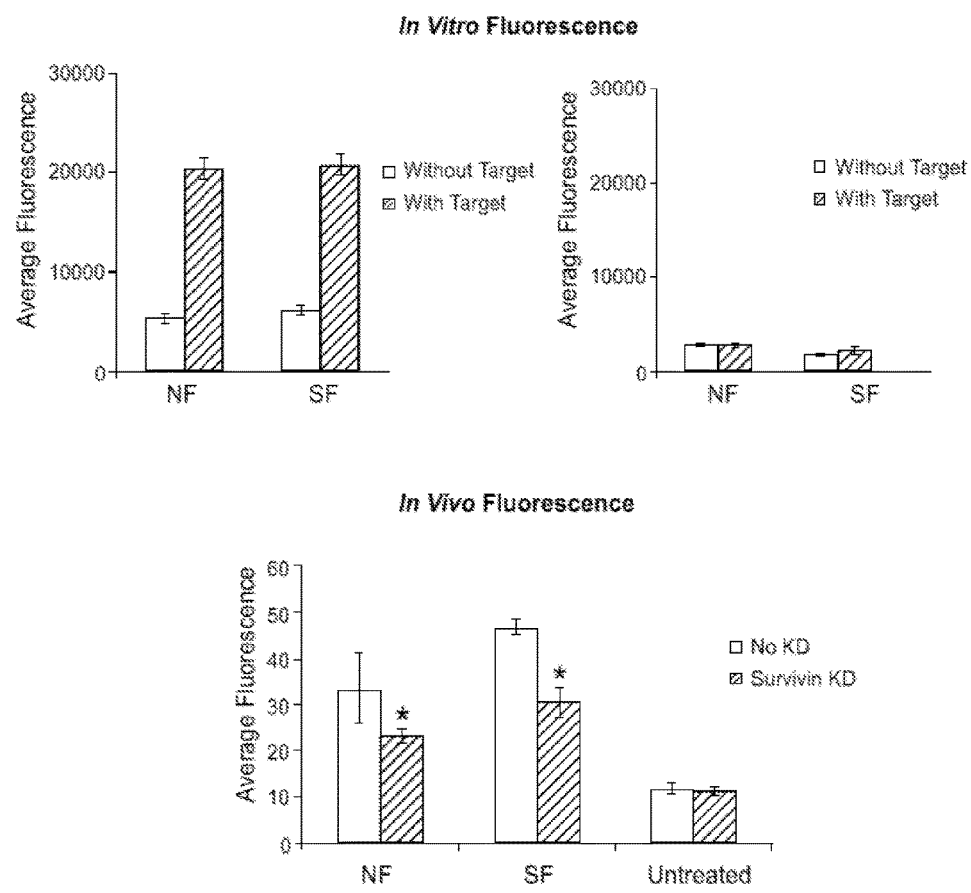
FIG. 6 depicts the detection of nucleic acid targets. A) left: upon addition of a complementary target, the StickyFlare (SF) elicits a fluorescence response comparable to the Nanoflare (NF). Right: Addition of a non-complementary target induces no response from either the NanoFlare or StickyFlare. B) Knockdown of Survivin mRNA is observable by the Nanoflare and StickyFlare by a corresponding reduction in average cell fluorescence.

To further evaluate the ability of SFs to detect the presence of nucleic acid targets in vitro, the fluorescence of 1 nM SFs in PBS was measured before and after the addition of 100 nM fully-complementary targets, and compared to that of previously-reported NanoFlares. A significant increase in fluorescence was observed upon the addition of the complementary target for both constructs (FIG. 6, upper left panel), but not observed with the addition of a scrambled target (FIG. 6, upper right panel). This indicated that the SF, like the NF is capable of detecting the presence of nucleic acid targets with sequence-specific discrimination. In order to evaluate the ability of the SF to quantify relative mRNA expression in vivo, HeLa cells were subjected to varying amounts of siRNA to knock down the oncogene survivin, then treated with SFs or NFs targeted to that gene. The resultant fluorescence in each cell was evaluated by flow cytometry (FIG. 6, lower panel). Increasing concentrations of anti-survivin siRNA corresponded with decreased fluorescence with both the NF and SF, indicating that both constructs were capable of detecting knockdown of the gene. Importantly, in all cases the addition of Stickyflares had no apparent effect on cell viability, as is consistent with SNA constructs.

Figure 7:
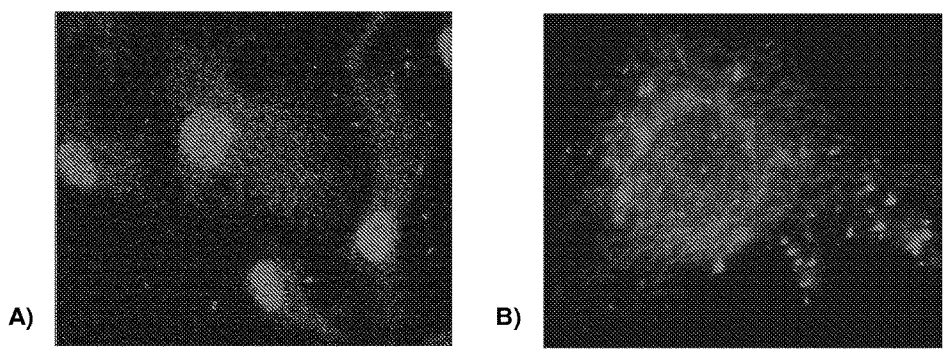
FIG. 7 shows the intracellular localization of KRAS mRNA. A) Fixed and permeabilized cells treated with KRAS SFs show a filamentous fluorescence pattern. B) the same filamentous pattern is observed in live cells.

The ability of the Stickyflare to observe spatial distribution of intracellular mRNA was also evaluated in HeLa cells using KRAS-targeting probes. First, basic mRNA hybridization was observed by treating fixed, permeabilized cells with SFs and observing the resultant intracellular fluorescence. The pattern of fluorescence recapitulated previously recorded filamentous distribution of KRAS mRNA, which is indicative of mitochondrial localization (FIG. 5, left panel; FIG. 7A) [Santangelo et al., Nucleic Acids Research 32: e57 (2004); Santangelo et al., BIOMEDO 10: 044025 (2005)]. Importantly, when this experiment was repeated using live cells by adding SFs to the growth medium with Stickyflares, the pattern of fluorescence was similar, indicating mitochondrial colocalization of the SFs in live cells (FIG. 5, left panel; FIG. 7B).

CONCLUSION: The intracellular localization of RNA often has a significant impact on the function of transcripts, and on the cell as a whole. The evaluation of RNA distribution in live cells required sophisticated and/or damaging transfection techniques such as microinjection. In contrast, SNAs are capable of entering live cells with high efficiency and minimal toxicity, and can bind with high specificity to targeted transcripts. The development of the StickyFlare takes advantages of these features to form the first construct capable of facile, non-toxic in situ hybridization to be used in either live or fixed cells. It is demonstrated herein that the StickyFlare is capable of quantifying relative mRNA expression in live cells, and can track changes in the spatial distribution of transcripts over time to gain a more complete understanding of the dynamics of gene expression.

What is claimed is:

1. A method comprising:
contacting a target polynucleotide with a composition comprising a nanoparticle under conditions that allow association of the target polynucleotide with the nanoparticle;
the nanoparticle comprising a first polynucleotide attached thereto, wherein a portion of the first polynucleotide comprises a sequence that is identical to a portion of the target polynucleotide;
the nanoparticle further comprising a second polynucleotide, wherein the second polynucleotide:
  (i) comprises a marker;
  (ii) is hybridized to the first polynucleotide; and
  (iii) wherein hybridization of the second polynucleotide to the first polynucleotide results in an overhang of the second polynucleotide, wherein the overhang is from about 2 to about 30 nucleotides in length;
wherein association of the target polynucleotide and the nanoparticle results in:
  (i) release of the second polynucleotide from the nanoparticle; and
  (ii) association of the second polynucleotide and the target polynucleotide;
the association causing a detectable signal.

2. The method of claim 1, wherein the position of the signal is determined.

3. The method of claim 1, wherein the detectable signal is measured at time X and at time Y, wherein time Y is subsequent to time X.

4. The method of claim 3, wherein the position of the signal is determined at time X and at time Y.

5. The method of claim 4, wherein the change in position between time X and time Y is determined.

6. The method of claim 1, wherein the detectable signal is measured in vitro.

7. The method of claim 1, wherein the detectable signal is measured in a cell.

8. The method of claim 7, wherein the cell is fixed and permeabilized.

9. The method of claim 1, wherein the first polynucleotide and/or the second polynucleotide is DNA.

10. The method of claim 1, wherein the first polynucleotide and/or the second polynucleotide is RNA.

11. The method of claim 1, wherein the marker is quenched when the second polynucleotide comprising the marker is hybridized to the first polynucleotide.

12. The method of claim 1, wherein the second polynucleotide comprises a marker which is a detectable label, wherein the marker is detectable only when the second polynucleotide is associated with the target polynucleotide.

13. The method of claim 1, wherein the nanoparticle comprises a multiplicity of first polynucleotides and a multiplicity of second polynucleotides.

14. The method of claim 13 wherein at least one polynucleotide in the multiplicity of second polynucleotides associates with a different target polynucleotide than at least one other polynucleotide in the multiplicity of second polynucleotides.

15. The method of claim 1, wherein the target polynucleotide is a non-coding RNA.

16. The method of claim 15, wherein the non-coding RNA is a piwi-interacting RNA (piRNA).

17. The method of claim 1, wherein the composition further comprises a therapeutic agent.

18. The method of claim 1 wherein the second polynucleotide hybridizes over the entire length of the first polynucleotide.

19. The method of claim 1 wherein the nanoparticle comprises about 10 second polynucleotides.

20. The method of claim 1 wherein the difference in melting temperature ($T_m$) between the first polynucleotide and the second polynucleotide is about 20-25° C.

21. The method of claim 1 wherein the nanoparticle comprises gold, silver copper, or platinum.

22. The method of claim 21 wherein the nanoparticle comprises gold.

* * * * *

SEQUENCE LISTING

<160> NUMBER OF SEQ ID NOS: 16

<210> SEQ ID NO 1
<211> LENGTH: 22
<212> TYPE: DNA
<213> ORGANISM: Artificial Sequence
<220> FEATURE:
<223> OTHER INFORMATION: Synthetic Primer

<400> SEQUENCE: 1
cgtctacctt cgcgcaaaaa aa                                              22

<210> SEQ ID NO 2
<211> LENGTH: 26
<212> TYPE: DNA
<213> ORGANISM: Artificial Sequence
<220> FEATURE:
<223> OTHER INFORMATION: Synthetic Primer

<400> SEQUENCE: 2
gcgcgaaggt aggcggagtc ggtcga                                          26

<210> SEQ ID NO 3

```
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
ccggcatgtg caaaaaaaaa                                                    20

<210> SEQ ID NO 4
<211> LENGTH: 28
<212> TYPE: DNA
<213> ORGANISM: Artificial Sequence
<220> FEATURE:
<223> OTHER INFORMATION: Synthetic Primer

<400> SEQUENCE: 4
ttgcacatgc cggagccgtt gtcgacga                                           28

<210> SEQ ID NO 5
<211> LENGTH: 28
<212> TYPE: DNA
<213> ORGANISM: Artificial Sequence
<220> FEATURE:
<223> OTHER INFORMATION: Synthetic Primer

<400> SEQUENCE: 5
tcgtcgacaa cggctccggc atgtgcaa                                           28

<210> SEQ ID NO 6
<211> LENGTH: 22
<212> TYPE: DNA
<213> ORGANISM: Artificial Sequence
<220> FEATURE:
<223> OTHER INFORMATION: Synthetic Primer

<400> SEQUENCE: 6
cgtctacctt cgcgcaaaaa aa                                                 22

<210> SEQ ID NO 7
<211> LENGTH: 26
<212> TYPE: DNA
<213> ORGANISM: Artificial Sequence
<220> FEATURE:
<223> OTHER INFORMATION: Synthetic Primer

<400> SEQUENCE: 7
gcgcgaaggt aggcggagtc ggtcga                                             26

<210> SEQ ID NO 8
<211> LENGTH: 23
<212> TYPE: DNA
<213> ORGANISM: Artificial Sequence
<220> FEATURE:
<223> OTHER INFORMATION: Synthetic Primer

<400> SEQUENCE: 8
gcagcccttt ctcaagaaaa aaa                                                23

<210> SEQ ID NO 9
<211> LENGTH: 26
<212> TYPE: DNA
<213> ORGANISM: Artificial Sequence
<220> FEATURE:
<223> OTHER INFORMATION: Synthetic Primer

<400> SEQUENCE: 9
```
cttgagaaag ggctgccagg cagggg                                              26

<210> SEQ ID NO 10
<211> LENGTH: 26
<212> TYPE: DNA
<213> ORGANISM: Artificial Sequence
<220> FEATURE:
<223> OTHER INFORMATION: Synthetic Primer

<400> SEQUENCE: 10
cccctgcctg gcagccctttt ctcaag                                             26

<210> SEQ ID NO 11
<211> LENGTH: 22
<212> TYPE: DNA
<213> ORGANISM: Artificial Sequence
<220> FEATURE:
<223> OTHER INFORMATION: Synthetic Primer

<400> SEQUENCE: 11
gccctgtgtg aacctaaaaa aa                                                  22

<210> SEQ ID NO 12
<211> LENGTH: 25
<212> TYPE: DNA
<213> ORGANISM: Artificial Sequence
<220> FEATURE:
<223> OTHER INFORMATION: Synthetic Primer

<400> SEQUENCE: 12
aggttcacac agggcctggc cttgc                                               25

<210> SEQ ID NO 13
<211> LENGTH: 25
<212> TYPE: DNA
<213> ORGANISM: Artificial Sequence
<220> FEATURE:
<223> OTHER INFORMATION: Synthetic Primer

<400> SEQUENCE: 13
gcaaggccag gccctgtgtg aacct                                               25

<210> SEQ ID NO 14
<211> LENGTH: 20
<212> TYPE: DNA
<213> ORGANISM: Artificial Sequence
<220> FEATURE:
<223> OTHER INFORMATION: Synthetic Primer

<400> SEQUENCE: 14
ccggcatgtg caaaaaaaaa                                                     20

<210> SEQ ID NO 15
<211> LENGTH: 28
<212> TYPE: DNA
<213> ORGANISM: Artificial Sequence
<220> FEATURE:
<223> OTHER INFORMATION: Synthetic Primer

<400> SEQUENCE: 15
ttgcacatgc cggagccgtt gtcgacga                                            28

<210> SEQ ID NO 16
<211> LENGTH: 28
<212> TYPE: DNA

```
<213> ORGANISM: Artificial Sequence
<220> FEATURE:
<223> OTHER INFORMATION: Synthetic Primer

<400> SEQUENCE: 16
tcgtcgacaa cggctccggc atgtgcaa                                            28
```